United States Patent
Hatanaka et al.

(10) Patent No.: US 11,252,954 B2
(45) Date of Patent: Feb. 22, 2022

(54) METHOD FOR PRESERVING A CELL MATERIAL IN AN UNFROZEN STATE

(71) Applicant: NISSAN CHEMICAL CORPORATION, Tokyo (JP)

(72) Inventors: Daisuke Hatanaka, Funabashi (JP); Hisato Hayashi, Tokyo (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/645,540

(22) PCT Filed: Sep. 7, 2018

(86) PCT No.: PCT/JP2018/033198
§ 371 (c)(1),
(2) Date: Mar. 9, 2020

(87) PCT Pub. No.: WO2019/049985
PCT Pub. Date: Mar. 14, 2019

(65) Prior Publication Data
US 2020/0260719 A1    Aug. 20, 2020

(30) Foreign Application Priority Data
Sep. 8, 2017   (JP) .............................. JP2017-173479

(51) Int. Cl.
*A01N 1/02*   (2006.01)
(52) U.S. Cl.
CPC .................................. *A01N 1/021* (2013.01)
(58) Field of Classification Search
None
See application file for complete search history.

(56) References Cited

U.S. PATENT DOCUMENTS

| | | | |
|---|---|---|---|
| 10,519,419 B2 * | 12/2019 | Otani | ................... C12N 5/0025 |
| 2017/0009201 A1 | 1/2017 | Hayashi et al. | |
| 2018/0008646 A1 * | 1/2018 | Ishii | ..................... C12N 5/0068 |
| 2018/0136196 A1 | 5/2018 | Abe et al. | |

FOREIGN PATENT DOCUMENTS

| | | |
|---|---|---|
| EP | 2878664 A1 | 6/2015 |
| EP | 3098299 A1 | 11/2016 |
| EP | 3098306 A1 | 11/2016 |
| JP | 2005-312398 A | 11/2005 |
| WO | WO 2014/017513 A1 | 1/2014 |
| WO | WO 2015/111686 A1 | 7/2015 |
| WO | WO 2016/121896 A1 | 8/2016 |
| WO | WO 2016/167373 A1 | 10/2016 |

OTHER PUBLICATIONS

Japanese Patent Office, International Search Report in International Patent Application No. PCT/JP2018/033198 (dated Dec. 4, 2018).
European Patent Office, Extended European Search Report in European Patent Application No. 18854124.7 (dated Jul. 17, 2020).

* cited by examiner

*Primary Examiner* — Ralph J Gitomer
(74) *Attorney, Agent, or Firm* — Leydig, Voit & Mayer, Ltd.

(57) ABSTRACT

Cells or tissues are preserved in an unfrozen state in the liquid composition containing deacylated gellan gum or a salt thereof, and an acidic polysaccharide or a salt thereof capable of maintaining a random coil state in a divalent metal cation medium and cross-linking via a divalent metal ion. The acidic polysaccharide may be alginic acid. The liquid composition may further contain a metal cation such as calcium ion and the like.

6 Claims, 1 Drawing Sheet

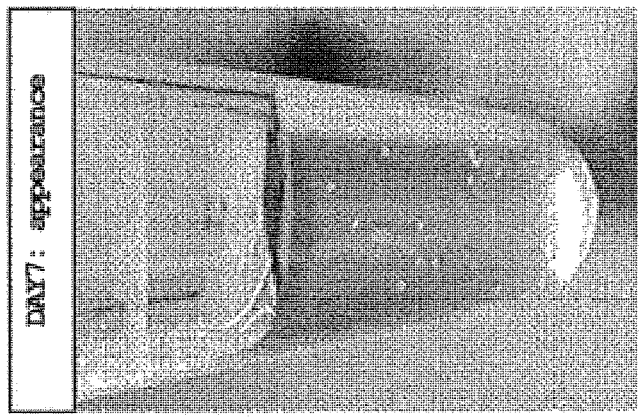
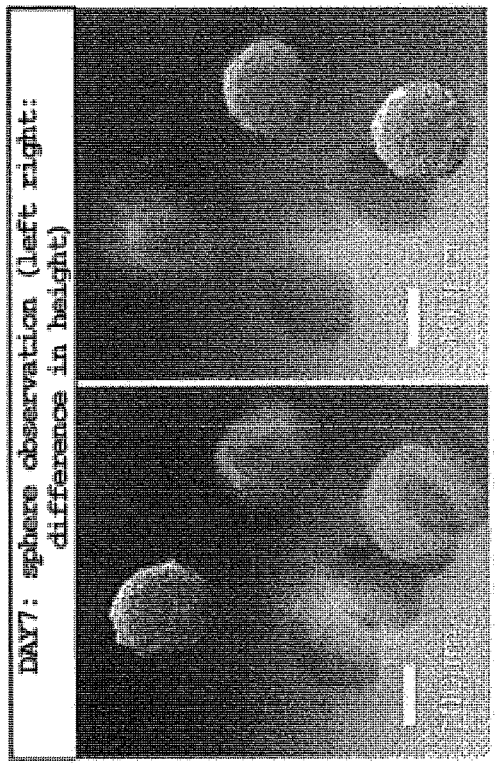
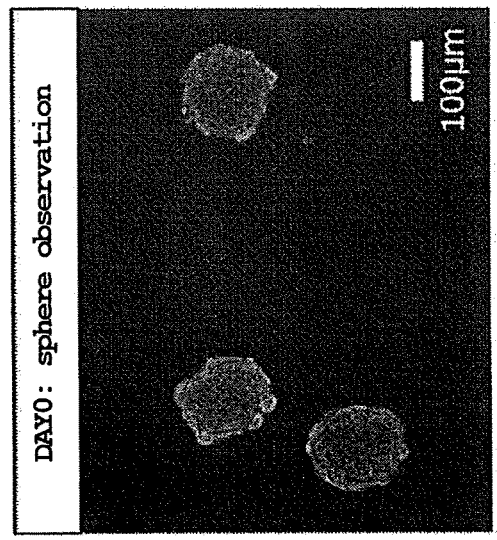

METHOD FOR PRESERVING A CELL MATERIAL IN AN UNFROZEN STATE

CROSS-REFERENCE TO RELATED APPLICATIONS

This patent application is the U.S. national phase of International Patent Application No. PCT/JP2018/033198, filed Sep. 7, 2018, which claims the benefit of Japanese Patent Application No. 2017-173479, filed on Sep. 8, 2017, which are incorporated by reference in their entireties herein.

TECHNICAL FIELD

The present invention relates to a liquid composition for preserving a cell or tissue in an unfrozen state, and a method for preserving a cell or tissue by the use of the liquid composition.

BACKGROUND ART

Currently, in transplantation therapy research using stem cells such as iPS cells, mesenchymal stem cells and the like, cell banks prepare a large amount of stem cells and cryopreserve same, and respective research institutions and medical institutions order desired stem cells in a cryopreserved state from the stock in the cell banks, thaw and wake them up, differentiate them into the desired cells as necessary, and subject them to various applications. However, in cell bank systems that operate autologous transplant systems and manage and store a large number of allogeneic cell stocks, which is expected to be realized in the future, it is difficult to stably supply a large amount of cells in a state suitable for transplantation with the current transportation technology that presumes freezing of cells. That is, at the time of transplantation, it is necessary to thaw cryopreserved cells, culture them and, when necessary, differentiate them into target cells, and then provide a large amount of cells in good condition. When cells must be transported in a frozen state, transplantation facilities must obtain frozen cells from cell banks that store and manage the cells, and perform large-scale cultivation on their own in the facilities. Therefore, transplantation facilities must have large-scale cultivation equipment (e.g., Cell Processing Center (CPC)). In facilities without such equipment, it is difficult to carry out transplantation therapy. On the other hand, cell banks usually have the technology and equipment to culture a large amount of cells, and therefore, if the cell banks can prepare a large amount of cells in a good state suitable for transplantation, and the obtained cells can be quickly supplied to the transplantation facility while maintaining the good state, then transplantation therapy can be performed even in facilities that do not have equipment for culturing a large amount of cells. To solve this problem, a technology to preserve and transport a large number of cells in good condition without freezing is essential.

Polysaccharides such as deacylated gellan gum (DAG) and the like form a three-dimensional network (amorphous structure) in water by assembling via a metal cation (e.g., divalent metal cation such as calcium ion and the like). When cells are cultured in a liquid medium containing the three-dimensional network, the cells in the medium are trapped in the three-dimensional network and do not sink. Therefore, the cells can be cultured while being uniformly dispersed in a suspended state without the need for shaking, rotating operation and the like (static suspension culture). In addition, it is possible to form the aforementioned three-dimensional network without substantially increasing the viscosity of the liquid medium. Therefore, a medium composition containing the three-dimensional network is also superior in the operability in passage culture and the like (patent document 1). This medium composition permitting static suspension culture has various superior properties such as promotion of proliferation activity of various cells and the like. Thus, its application to a wide range of technical fields such as regenerative medicine, large-scale production of protein and the like, and the like is expected.

Patent document 2 discloses that a medium composition containing a nanofiber is used for the preservation and transportation of cells and tissues.

DOCUMENT LIST

Patent Documents patent document 1: WO 2014/017513
patent document 2: WO 2015/111686

SUMMARY OF THE INVENTION

Problems to be Solved by the Invention

The present invention aims to provide a technique for preserving a cell or tissue in an unfrozen state while maintaining good survivability.

Means of Solving the Problems

The present inventors have conducted intensive studies in an attempt to solve the aforementioned problems and found that cells and tissues can be preserved for a long term at room temperature while maintaining good survivability by suspending them in a medium composition containing deacylated gellan gum and alginic acid. By preserving spheres in the medium composition, coagulation between the spheres can be avoided, and the development of necrosis in the inside of the spheres can be suppressed. In the medium composition, cells can be preserved for a long term at room temperature while maintaining good survivability even under vibrating conditions assuming the environment during transportation. Based on these findings, the present inventors studied further and completed the present invention.

That is, the present invention is as follows:

[1] A liquid composition for preserving a cell or tissue in an unfrozen state, comprising deacylated gellan gum or a salt thereof, and an acidic polysaccharide or a salt thereof capable of maintaining a random coil state in a divalent metal cation medium and cross-linking via a divalent metal ion.

[2] The liquid composition of [1], wherein a concentration of the deacylated gellan gum or a salt thereof in the liquid composition is 0.002-0.01 (w/v) % when converted to deacylated gellan gum in a free form, a concentration of the acidic polysaccharide or a salt thereof is 0.004-0.1 (w/v) % when converted to a free form, and a mass ratio of the acidic polysaccharide or a salt thereof to the deacylated gellan gum or a salt thereof is not less than 1 when converted to a free form.

[3] The liquid composition of [1] or [2], wherein the acidic polysaccharide is selected from the group consisting of alginic acid, pectin and pectic acid.

[4] The liquid composition of [3], wherein the aforementioned acidic polysaccharide is alginic acid.

[5] The liquid composition of any of [1] to [4], further comprising a metal cation.
[6] The liquid composition of [5], wherein the aforementioned metal cation is a calcium ion.
[7] The liquid composition of any of [1] to [6], wherein the aforementioned acidic polysaccharide or a salt thereof is treated by high-pressure vapor sterilization.
[8] A method for preserving a cell or tissue comprising preserving a cell or tissue in an unfrozen state in the liquid composition of any of [1] to [7].
[9] The method of [8], wherein the cell or tissue is preserved in a suspended state in the liquid composition.
[10] The method of [8] or [9], wherein the cell or tissue is preserved at 1° C.-30° C.
[11] The method of any of [8] to [10], wherein the cell or tissue is preserved in a closed container.
[12] The method of any of [8] to [11], wherein the cell or tissue is preserved in an environment accompanying vibration.
[13] The method of any of [8] to [12], wherein the cell to be preserved is in a sphere state.

Effect of the Invention

Using the liquid composition of the present invention, cells and tissues can be preserved in an unfrozen state at, for example, room temperature and the like while maintaining good survivability. When spheres are preserved in the liquid composition of the present invention, coagulation between the spheres can be avoided, and the development of necrosis in the inside of the spheres can be suppressed.

The liquid composition of the present invention is also useful for transportation of cells and tissues in an unfrozen state. For example, when cells are adherent cultured on a plate and transported as they are, the cells may be detached from the plate due to vibration during transportation, and the original function of the cells may be reduced. However, when the liquid composition of the present invention is used, cells and tissues can be maintained in a suspended state. Therefore, cell damage due to detachment from the plate and the like due to vibration during transportation can be avoided, and cells and tissues can be preserved and transported while maintaining the original function of the cells.

BRIEF DESCRIPTION OF THE DRAWINGS

FIG. 1 shows the form of spheres before and after preservation. The left FIGURE shows the form of spheres at the start of the preservation. The middle FIGURE shows the form of spheres after 7 days of preservation. The right FIGURE shows the spheres maintained in a suspended state after 7 days of preservation.

DESCRIPTION OF EMBODIMENTS

The present invention is described in more detail below.

Liquid Composition

The present invention provides a liquid composition for preserving a cell or tissue in an unfrozen state. The liquid composition makes it possible to preserve cells and tissues in an unfrozen state while maintaining survivability.

The cell in the present invention is a most basic unit constituting animals or plants, which has, as its elements, cytoplasm and various organelles inside the cellular membrane. In this case, the nucleus encapsulating the DNA may or may not be contained intracellularly. For example, the animal-derived m cells in the present invention include reproductive cells such as spermatozoon, oocyte and the like, somatic cells constituting the living body, stem cells, progenitor cells, cancer cells separated from the living body, cells separated from the living body, which acquired immortalizing ability and is maintained stably in vitro (cell line), cells separated from the living body and applied with artificial genetic modification, cells separated from the living body wherein the nucleus is artificially exchanged, and the like. Examples of the somatic cells constituting the living body include, but are not limited to, fibroblast, bone marrow cells, B lymphocytes, T lymphocytes, neutrophils, erythrocytes, platelets, macrophages, monocytes, osteocytes, bone marrow cells, pericytes, dendritic cells, keratinocytes, adipocytes, mesenchymal cells, epithelial cells, epidermal cells, endothelial cells, vascular endothelial cells, hepatocytes, chondrocytes, cumulus cells, neural cells, glial cells, neurons, oligodendrocytes, microglia, astrocytes, heart cells, esophagus cells, muscle cells (e.g., smooth muscle cells or skeletal muscle cells), pancreatic beta cells, melanin cells, hematopoietic progenitor cells, mononuclear cells and the like. The somatic cells include cells collected from any tissue, for example, skin, kidney, spleen, adrenal gland, liver, lung, ovary, pancreas, uterus, stomach, colon, small intestine, large intestine, bladder, prostate, testis, thymus, muscle, connective tissue, bone, cartilage, vascularized tissue, blood, heart, eye, brain, nerve tissue and the like. Stem cells are cells concurrently having an ability to replicate itself, and an ability to differentiate into other plural lineages. Examples thereof include, but are not limited to, embryonic stem cells (ES cell), embryonic tumor cells, embryonic germ stem cells, artificial pluripotent stem cells (iPS cell), neural stem cells, hematopoietic stem cells, mesenchymal stem cells, liver stem cells, pancreas stem cells, muscle stem cells, germ stem cells, intestinal stem cells, cancer stem cells, hair follicle stem cells and the like. Progenitor cells are cells on the way to differentiate from the aforementioned stem cell into a particular somatic cell or reproductive cell. Cancer cells are cells that are derived from a somatic cell and have acquired infinite proliferative capacity. Cell lines are cells that have acquired infinite proliferative capacity by an artificial operation in vitro, and examples thereof include, but are not limited to, CHO (Chinese hamster ovary cell line), HCT116, Huh7, HEK293 (human embryonic kidney cell), HeLa (human uterine cancer cell line), HepG2 (human liver cancer cell line), UT7/TPO (human leukemia cell line), MDCK, MDBK, BHK, C-33A, HT-29, AE-1, 3D9, Ns0/1, Jurkat, NIH3T3, PC12, S2, Sf9, Sf21, High Five (registered trade mark), Vero and the like.

The plant-derived cell in the present invention also includes cells separated from each tissue of a plant body, as well as a protoplast obtained by artificially removing the cell wall from the cell.

The tissue in the present invention is a unit of a structure which is an assembly in a certain manner of cells having some kinds of different properties and functions, and examples of the animal tissue include epithelial tissue, connective tissue, muscular tissue, nerve tissue and the like. Examples of the plant tissue include meristem, epidermis tissue, assimilation tissue, mesophyll tissue, conductive tissue, mechanical tissue, parenchyma tissue, dedifferentiated cell cluster (callus) and the like.

The cell or tissue to be preserved in the liquid composition of the present invention can be selected freely from the cells or tissues described above. The cells or tissues can be directly recovered from an animal or plant body. The cells or tissues may be induced, grown or transformed from m an animal or plant body by applying a particular treatment and then collected. In this case, the treatment may be in vivo or in vitro. Examples of the animal include fish, amphibian, reptiles, birds, pancrustacea, hexapoda, mammals and the like. Examples of the mammal include, but are not limited to, rat, mouse, rabbit, guinea pig, squirrel, hamster, vole, platypus, dolphin, whale, dog, cat, goat, bovine, horse, sheep, swine, elephant, common marmoset, squirrel monkey, Macaca mulatta, chimpanzee and human. The plant is not particularly limited as long as the collected cells or tissues can be applied to liquid culture. Examples thereof include, but are not limited to, plants producing crude drugs (e.g., saponin, alkaloids, berberine, scopolin, phytosterol etc.) (e.g., ginseng, periwinkle, henbane, coptis, belladonna etc.), plants producing dye or polysaccharide to be a starting material for cosmetic or food (e.g., anthocyanin, safflower dye, madder dye, saffron dye, flavones etc.) (e.g., blueberry, safflower, madder, saffron etc.), or plants producing a pharmaceutical active pharmaceutical ingredient and the like.

In a preferable embodiment, the liquid composition of the present invention makes it possible to preserve viable cells and tissues in an unfrozen state while maintaining a suspended state.

Suspending of cells or tissues in the present invention refers to a state where cells or tissues do not adhere to a preservation or culture container (non-adhesive). Furthermore, in the present invention, when the cells or tissues are preserved in a liquid composition, the state where the cells or tissues are uniformly dispersed and suspended in the liquid composition in the absence of a pressure on or vibration of the liquid composition from the outside or shaking, rotating operation and the like in the composition is referred to as "static suspension", and preservation of the cells or tissues in such condition is referred to as "static suspension preservation". In the "static suspension", the period of suspending includes not less than 5 min (e.g., at least 5-60 min), not less than 1 hr (e.g., 1 hr-24 hr), not less than 24 hr (e.g., 1 day-21 days), not less than 48 hr, not less than 7 days etc., though the period is not limited thereto as long as the suspended state is maintained.

in a liquid composition to be evaluated at a concentration of $2 \times 10^4$ cells/ml, injecting 10 ml thereof in a 15 ml conical tube, standing the tube for at least not less than 5 min (e.g., not less than 1 hr, not less than 24 hr, not less than 48 hr, not less than 7 days) at desired temperature (e.g., 25° C., 37° C.), and observing whether the suspended state of the cells is maintained. When not less than 70% of the total cells are in a suspended state, it is concluded that the suspended state was maintained. Polystyrene beads (Size 500-600 μm, manufactured by Polysciences Inc.) may be used for evaluation instead of the cells The liquid composition of the present invention contains deacylated gellan gum or a salt thereof, and an acidic polysaccharide or a salt thereof capable of maintaining a random coil state in a divalent metal cation medium and cross-linking via a divalent metal ion. The liquid composition of the present invention containing deacylated gellan gum or a salt thereof, and an acidic polysaccharide or a salt thereof capable of maintaining a random coil state in a divalent metal cation medium and cross-linking via a divalent metal ion can preserve a cell or tissue in an unfrozen state while maintaining good survivability. In a preferable embodiment, the liquid composition of the present invention containing deacylated gellan gum or a salt thereof, and an acidic polysaccharide or a salt thereof capable of maintaining a random coil state in a divalent metal cation medium and cross-linking via a divalent metal ion is provided with the property enabling preservation of cells and tissues in a suspended state (preferably, static suspension preservation) (effect of maintaining the suspended state of cells and tissues).

The deacylated gellan gum is a linear polymer polysaccharide containing 4 molecules of sugars of 1-3 bonded glucose, 1-4 bonded glucuronic acid, 1-4 bonded glucose and 1-4 bonded rhamnose as the constituent unit, which is a polysaccharide represented by the following formula (I) wherein $R_1$, $R_2$ are each a hydrogen atom, and n is an integer of two or more. $R_1$ may contain a glyceryl group, $R_2$ may contain an acetyl group, and the content of the acetyl group and glyceryl group is preferably not more than 10%, more preferably not more than 1%.

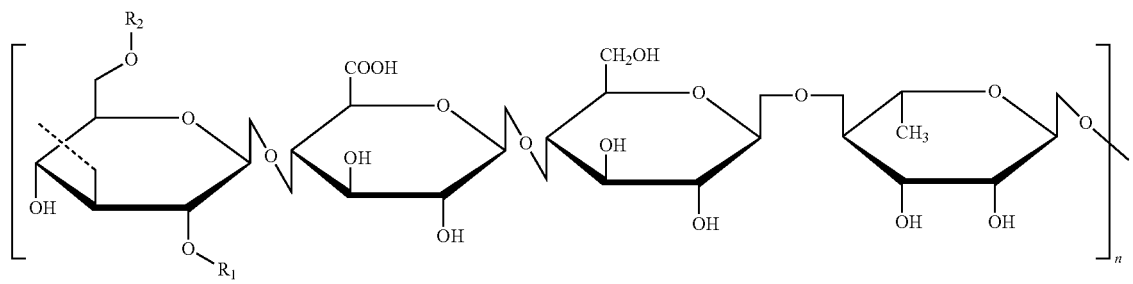

(I)

In a preferable embodiment, the liquid composition of the present invention permits static suspension of cells or tissues at least on one point in the temperature range capable of preserving cells or tissues in an unfrozen state (e.g., 0-37° C.). The liquid composition of the present invention permits static suspension of cells or tissues at least on one point in the temperature range of preferably 1-30° C., more preferably 15-30° C., further preferably 22-28° C., further more preferably 24-26° C., most preferably at least 25° C.

Whether static suspension is possible can be evaluated by, for example, uniformly dispersing the cells to be preserved Deacylated gellan gum can be produced by culturing a gellan gum producing microorganism in a fermentation medium, subjecting a mucosal product produced outside fungal body to an alkali treatment, deacylating and recovering the glyceryl group and the acetyl group bonded to 1-3 bonded glucose residue and, after steps of drying, pulverization and the like, powderizing the product. Examples of the purification method include liquid-liquid extraction, fractional precipitation, crystallization, various kinds of ion exchange chromatography, gel filtration chromatography using Sephadex LH-20 and the like, adsorption chromatography using activated carbon, silica gel and the like, adsorption and desorption treatment of active substance by thin layer chromatography, high performance liquid chromatography using reversed-phase column and the like, and impurity can be removed and the compound can be purified by using them singly or in combination in any order, or repeatedly. Examples of the gellan gum-producing microorganism include, but are not limited to, Sphingomonas elodea and microorganisms obtained by modifying the gene of Sphingomonas elodea.

As the deacylated gellan gum, a phosphorylated one can also be used. The phosphorylation can be performed by a known method.

A deacylated gellan gum derivative of a compound represented by the formula (I) wherein a hydroxyl group for $R_1$ and/or $R_2$ is substituted by $C_{1-3}$ alkoxy group, $C_{1-3}$ alkylsulfonyl group, a monosaccharide residue such as glucose, fructose and the like, oligosaccharide residue such as sucrose, lactose and the like, or amino acid residue such as glycine, arginine and the like can also be used in the present invention. In addition, the deacylated gellan gum can also be crosslinked using a crosslinker such as 1-ethyl-3-(3-dimethylaminopropyl)carbodiimide (EDC) and the like.

Examples of the salt include alkali metal salts such as lithium, sodium, potassium; alkaline earth metal salts such as calcium, barium, magnesium; salts such as aluminum, zinc, copper, iron and the like; ammonium salt; quaternary ammonium salts such as tetraethylammonium, tetrabutylammonium, methyltributylammonium, cetyltrimethylammonium, benzylmethylhexyldecylammonium, choline and the like; salts with organic amines such as pyridine, triethylamine, diisopropylamine, ethanolamine, diolamine, tromethamine, meglumine, procaine, chloroprocaine and the like; salts with amino acid such as glycine, alanine, valine and the like; and the like.

The weight average molecular weight of deacylated gellan gum or a salt thereof is preferably 10,000 to 50,000,000, more preferably 100,000 to 20,000,000, still more preferably 1,000,000 to 10,000,000. For example, the molecular weight can be measured based on pullulan by gel penetration chromatography (GPC).

As deacylated gellan gum or a salt thereof, commercially available products, for example, "KELCOGEL (registered trade mark of CP Kelco) CG-LA" manufactured by SANSHO Co., Ltd., "KELCOGEL (registered trade mark of CP Kelco)" manufactured by San-Ei Gen F.F.I., Inc. and the like can be used.

Examples of the acidic polysaccharide or a salt thereof capable of maintaining a random coil state in a divalent metal cation (e.g., calcium ion, magnesium ion, barium ion, copper ion, iron ion, zinc ion, tin ion, lead ion etc., preferably calcium ion) medium and cross-linking via a divalent metal ion include alginic acid, pectin, pectin acid, a salt thereof and the like, with preference given to alginic acid or a salt thereof.

Alginic acid is a polysaccharide having a structure in which both uronic acids of α1-4 bonded L-glucuronic acid and β1-4 bonded D-mannuronic acid are straight-chain polymerized.

Alginic acid and a salt thereof can be extracted and is purified from brown algae represented by kelp and wakame by an ion exchange reaction of a carboxyl group of alginic acid. The alginic acid in the alga body is in an insoluble salt with polyvalent cation such as calcium ion and the like. Thus, this is ion exchanged with Na to give water-soluble sodium alginate which is extracted outside the alga body. Furthermore, an acid is added to an aqueous solution of sodium alginate to cause coagulation and precipitation of insoluble alginic acid, and the coagulated and precipitated alginic acid is isolated to give purified alginic acid.

Examples of the salt include alkali metal salts such as lithium, sodium, potassium; alkaline earth metal salts such as calcium, barium, magnesium; salts such as aluminum, zinc, copper, iron and the like; ammonium salt; quaternary ammonium salts such as tetraethylammonium, tetrabutylammonium, methyltributylammonium, cetyltrimethylammonium, benzylmethylhexyldecylammonium, choline and the like; salts with organic amines such as pyridine, triethylamine, diisopropylamine, ethanolamine, diolamine, tromethamine, meglumine, procaine, chloroprocaine and the like; salts with amino acid such as glycine, alanine, valine and the like; and the like. In the present invention, sodium alginate is preferably used from the aspect of solubility in water.

The weight average molecular weight of alginic acid or a salt thereof is preferably 300 to 50,000,000, more preferably 500 to 10,000,000, still more preferably 1,000 to 5,000,000. For example, the molecular weight can be measured based on pullulan by gel penetration chromatography (GPC).

As alginic acid or a salt thereof, a commercially available product, for example, the following product can also be used.

KIMICA Corporation:
  KIMICA ALGIN Series IL-2, IL-6, I-1, I-3, I-5, I-8, ULV-L3, ULV-L5, ULV-1, ULV-3, ULV-5, ULV-20, ULV-L3G, IL-6G, I-1G, I-3G, IL-6M, BL-2, BL-6, B-1, B-3, B-5, B-8, SKAT-ONE, SKAT-ULV
  Algitechs Series LL, L, M, H
Kikkoman Biochemifa Company:
  DUCK ALGIN NSPH2R, NSPHR, NSPMR, NSPLR, NSPLLR
SANSHO Co., Ltd.:
  SUKOGIN, SAN-ALGIN
Hokkaido Mitsui Chemicals, Inc.:
  Alginic acid oligosaccharide ALGIN Deacylated gellan gum, and an acidic polysaccharide capable of maintaining a random coil state in a divalent metal cation medium and cross-linking via a divalent metal ion may be present in the form of tautomer, geometric isomer, a mixture of tautomers and geometric isomers, or mixtures thereof formed by isomerization in the ring or outside the ring. When deacylated gellan gum and an acidic polysaccharide capable of maintaining a random coil state in a divalent metal cation medium and cross-linking via a divalent metal ion have an asymmetric center, irrespective of whether the compounds are formed by isomerization, they may be present in the form of a resolved optical isomer or a mixture containing same at any ratio.

Deacylated gellan gum or a salt thereof, and an acidic polysaccharide or a salt thereof capable of maintaining a random coil state in a divalent metal cation medium and cross-linking via a divalent metal ion form a three-dimensional network (amorphous structure) by assembling via a metal cation (e.g., divalent metal cation such as calcium ion and the like) in the liquid composition. It is known that polysaccharides form a microgel via a metal cation (e.g., JP-A-2004-129596), and the aforementioned amorphous structure also includes such microgel as one embodiment. One embodiment of the assembly of deacylated gellan gum or a salt thereof, and an acidic polysaccharide or a salt thereof capable of maintaining a random coil state in a divalent metal cation medium and cross-linking via a divalent metal ion is a film structure. The liquid composition of the present invention contains a three-dimensional network (amorphous structure) formed by an assembly of deacylated gellan gum or a salt thereof, and an acidic polysaccharide or a salt thereof capable of maintaining a random coil state in a divalent metal cation medium and cross-linking via a divalent metal ion via a metal cation (e.g., divalent metal cation such as calcium ion and the like). When cells or tissues are suspended and preserved in the liquid composition of the present invention, the cells or tissues suspended in the liquid composition are trapped in the three-dimensional network and do not form sediments. Therefore, the cells or tissues can be preserved while being uniformly dispersed in a suspended state (static suspension preservation) without the need for shaking, rotating operation and the like. The liquid composition of the present invention in a preferable embodiment contains the aforementioned three-dimensional network (amorphous structure) in a uniformly dispersed state.

In a preferable embodiment, formation of the above-mentioned three-dimensional network (amorphous structure) does not substantially increase the viscosity of the medium composition of the present invention. The "without substantially increasing the viscosity of the liquid composition" means that the viscosity of the liquid composition does not exceed 8 mPa·s. In this case, the viscosity of the liquid composition is not more than 8 mPa·s, preferably not more than 4 mPa·s, more preferably not more than 2 mPa·s, at 25° C.

The viscosity of the liquid composition can be measured, for example, by the method described in the below-mentioned Examples. Specifically, it can be measured under 25° C. conditions and using an E-type viscosity meter (manufactured by Toki Sangyo Co., Ltd., TV-22 type viscosity meter, model: TVE-22 L, corn roter: standard roter 1° 34'xR24, rotating speed 100 rpm).

The liquid composition of the present invention may contain "deacylated gellan gum or a salt thereof, and an acidic polysaccharide or a salt thereof capable of maintaining a random coil state in a divalent metal cation medium and cross-linking via a divalent metal ion" other than polysaccharides or a salt thereof. The polysaccharide is preferably an acidic polysaccharide having an anionic functional group. The acidic polysaccharide is not particularly limited as long as it has an anionic functional group in the structure thereof, and includes, for example, polysaccharides having a uronic acid (e.g., glucuronic acid, iduronic acid, galacturonic acid, mannuronic acid), polysaccharides having a sulfate group or a phosphate group in a part of the structure thereof, and polysaccharides having the both structures, and includes not only naturally-obtained polysaccharides but also polysaccharides produced by microorganisms, polysaccharides produced by genetic engineering, and polysaccharides artificially synthesized using an enzyme. More specifically, examples thereof include hyaluronic acid, native gellan gum, rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate and a salt thereof.

The concentration (converted to deacylated gellan gum in free form) of deacylated gellan gum or a salt thereof in the liquid composition of the present invention is, for example, 0.002-0.01 (w/v) %, preferably 0.002-0.009 (w/v) %, more preferably 0.003-0.009 (w/v) %, further more preferably 0.0033-0.0066 (w/v) %.

The concentration (converted to free form) of the acidic polysaccharide (e.g., alginic acid) or a salt thereof capable of maintaining a random coil state in a divalent metal cation medium and cross-linking via a divalent metal ion in the liquid composition of the present invention is, for example, 0.004-0.1 (w/v) %, preferably 0.004-0.02 (w/v) %, more preferably 0.004-0.015 (w/v) %, further preferably 0.005-0.015 (w/v) %, further more preferably 0.0066-0.0133 (w/v) %.

The concentration of the deacylated gellan gum or a salt thereof is preferably not less than 0.002 (w/v) %, preferably not less than 0.003 (w/v) %, to ensure a sufficient action to suspend the cells or tissues. On the other hand, when the concentration is too high, the suspending action may become strong to lower the cell recovery rate and handling property of the medium itself. Therefore, it is not more than 0.01 (w/v) %, preferably not more than 0.009 (w/v) %. The concentration of the acidic polysaccharide (e.g., alginic acid) or a salt thereof capable of maintaining a random coil state in a divalent metal cation medium and cross-linking via a divalent metal ion is preferably not less than 0.004 (w/v) %, preferably not less than 0.005 (w/v) %, to ensure the property of rapidly losing the effect of maintaining the suspended state of the cells or tissues by a shear force (fragility of the effect of maintaining the suspended state of the cells or tissues to shear force). On the other hand, when the concentration is too high, gelation may occur. It is preferably not more than 0.1 (w/v) %, preferably not more than 0.02 (w/v) %, more preferably not more than 0.015 (w/v) %.

The mass ratio (converted to free form) of the deacylated gellan gum or a salt thereof and the acidic polysaccharide (e.g., alginic acid) or a salt thereof capable of maintaining a random coil state in a divalent metal cation medium and cross-linking via a divalent metal ion, which are contained in the liquid composition the present invention, is not less than 1 part by mass, preferably not less than 2 parts by mass, of the acidic polysaccharide (e.g., alginic acid) or a salt thereof capable of maintaining a random coil state in a divalent metal cation medium and cross-linking via a divalent metal ion per 1 part by mass of deacylated gellan gum or a salt thereof, to achieve the property of rapidly losing the effect of maintaining the suspended state of the cells or tissues by a shear force. In one embodiment, for example, 1-4 parts by mass, preferably 1-3 parts by mass, more preferably 1-2 parts by mass, of the acidic polysaccharide (e.g., alginic acid) or a salt thereof capable of maintaining a random coil state in a divalent metal cation medium and cross-linking via a divalent metal ion is used per 1 part by mass of deacylated gellan gum or a salt thereof.

The concentration of the compound in the liquid composition can be calculated by the following formula.

$$\text{Concentration}[\% \text{ (W/V)}] = \text{mass (g) of compound}/\text{volume (ml) of liquid composition} \times 100$$

The liquid composition of the present invention containing deacylated gellan gum or a salt thereof, and an acidic polysaccharide (e.g., alginic acid) or a salt thereof capable of maintaining a random coil state in a divalent metal cation medium and cross-linking via a divalent metal ion at the above-mentioned contents affords the effect of maintaining good survivability of the cells or tissues preserved in an unfrozen state. The liquid composition of the present invention containing deacylated gellan gum or a salt thereof, and an acidic polysaccharide (e.g., alginic acid) or a salt thereof capable of maintaining a random coil state in a divalent metal cation medium and cross-linking via a divalent metal ion at the above-mentioned contents affords the effect of maintaining the suspended state of the cells or tissues.

The liquid composition of the present invention containing deacylated gellan gum or a salt thereof, and an acidic polysaccharide (e.g., alginic acid) or a salt thereof capable of maintaining a random coil state in a divalent metal cation medium and cross-linking via a divalent metal ion at the above-mentioned contents also has property of rapidly losing the effect of maintaining the suspended state of the cells or tissues by a shear force such as pipetting, filter filtration and the like (fragility of the effect of maintaining the suspended state of the cells or tissues to shear force).

The liquid composition of the present invention contains the three-dimensional network (amorphous structure) formed by an assembly of deacylated gellan gum or a salt thereof, and an acidic polysaccharide (e.g., alginic acid) or a salt thereof capable of maintaining a random coil state in a divalent metal cation medium and cross-linking via a divalent metal ion, via a metal cation (e.g., divalent metal cation such as calcium ion and the like), and this affords the effect of maintaining the suspended state of the cells or tissues. Due to the presence of an acidic polysaccharide (e.g., alginic acid) or a salt thereof capable of maintaining a random coil state in a divalent metal cation medium and cross-linking via a divalent metal ion, the three-dimensional network is fragile to a chelating agent or shear force and the three-dimensional network is easily destroyed by a shear force by pipetting, filter filtration and the like. As a result, the effect of maintaining the suspended state of the cells or tissues is rapidly lost. Deacylated gellan gum contains a constituent unit having a comparatively linear structure. A plurality of deacylated gellan gum chains are bundled in the liquid composition to form a tight and stable three-dimensional network. This three-dimensional network is difficult to be destroyed by chelating agent, pipetting, filter filtration and the like. In contrast, when an acidic polysaccharide (e.g., alginic acid) or a salt thereof capable of maintaining a random coil state in a divalent metal cation medium and cross-linking via a divalent metal ion having a comparatively bulky structure due to the presence of both uronic acids of α1-4 bonded L-glucuronic acid and β1-4 bonded D-mannuronic acid is added to the liquid composition, bundling of the deacylated gellan gum is suppressed. As a result, the three-dimensional network is considered to become fragile to a shear force by pipetting, filter filtration and the like, though not particularly bound by the theory.

As mentioned above, in the liquid composition of the present invention, deacylated gellan gum or a salt thereof, and an acidic polysaccharide (e.g., alginic acid) or a salt thereof capable of maintaining a random coil state in a divalent metal cation medium and cross-linking via a divalent metal ion assemble via a metal cation (e.g., divalent metal cation such as calcium ion and the like) in the liquid medium to form a three-dimensional network (amorphous structure). Thus, the liquid composition of the present invention contains metal cations, for example, divalent metal cations (calcium ion, magnesium ion, zinc ion, iron ion and copper ion etc.), preferably calcium ion. Two or more kinds of metal cations can be used in combination, for example, calcium ion and magnesium ion, calcium ion and zinc ion, calcium ion and iron ion, and calcium ion and copper ion. Those of ordinary skill in the art can appropriately determine the combination. The metal cation concentration in the liquid composition of the present invention is, but is not limited to, 0.1 mM-300 mM, preferably 0.5 mM-100 mM.

The destruction of the three-dimensional network (the loss of the property to maintain the suspended state of the cells or tissues) by a shear force by pipetting, filter filtration and the like is a reversible reaction. Fragments of the three-dimensional network (amorphous structure) destroyed by the shear force assemble again via a metal cation (e.g., divalent metal cation such as calcium ion and the like) and regenerate a three-dimensional network (amorphous structure).

The liquid composition of the present invention preferably contains a medium (preferably liquid medium) used for culturing cells or tissues to be preserved. In this case, the liquid composition of the present invention can be prepared by mixing a medium (preferably liquid medium) used for culturing cells or tissues to be preserved and deacylated gellan gum or a salt thereof, and an acidic polysaccharide (e.g., alginic acid) or a salt thereof capable of maintaining a random coil state in a divalent metal cation medium and cross-linking via a divalent metal ion.

Examples of the medium used in culturing cells or tissues derived from animal (e.g., mammal) include Leibovitz's L-15 Medium, Dulbecco's Modified Eagle's Medium (DMEM), hamF12 medium (Ham's Nutrient Mixture F12), DMEM/F12 medium, McCoy's 5A medium, Eagle MEM medium (Eagle's Minimum Essential Medium; EMEM), αMEM medium (alpha Modified Eagle's Minimum Essential Medium; αMEM), MEM medium (Minimum Essential Medium), RPMI1640 medium, Iscove's Modified Dulbecco's Medium (IMDM), MCDB131 medium, William medium E, IPL41 medium, Fischer's medium, NutriStem MSC XF (manufactured by Biological Industries Ltd.), NutriStem hPSC XF (manufactured by Biological Industries Ltd.), StemPro34 (manufactured by Invitrogen), X-VIVO 10 (manufactured by Cambrex Corporation), X-VIVO 15 (manufactured by Cambrex Corporation), HPGM (manufactured by Cambrex Corporation), StemSpan H3000 (manufactured by STEMCELL Technologies), StemSpanSFEM (manufactured by STEMCELL Technologies), Stemlinell (manufactured by Sigma Aldrich), QBSF-60 (manufactured by Qualitybiological), StemProhESCSFM (manufactured by Invitrogen), mTeSR1 or 2 medium (manufactured by STEMCELL Technologies), Sf-900II (manufactured by Invitrogen), Opti-Pro (manufactured by Invitrogen), HFDM-1 (manufactured by NIPRO), NIPRO EIDF (manufactured by NIPRO), BMPro (manufactured by NIPRO) and the like.

When the cells or tissues are derived from a plant, a medium obtained by adding auxins and, where necessary, a plant growth control substance (plant hormone) such as cytokinins and the like at a suitable concentration to a basic medium such as Murashige Skoog (MS) medium, Linsmaier Skoog (LS) medium, White medium, Gamborg's B5 medium, niche medium, Hela medium, Morel medium and the like generally used for culture of plant tissues, or a modified medium wherein these medium components are modified to an optimal concentration (e.g., ammonia nitrogen at a half concentration etc.) can be mentioned as the medium. These media can be further supplemented, where necessary, with casein degrading enzyme, corn steep liquor, vitamins and the like. Examples of the auxins include, but are not limited to, 3-indoleacetic acid (IAA), 3-indolebutyric acid (IBA), 1-naphthaleneacetic acid (NAA), 2,4-dichlorophenoxyacetic acid (2,4-D) and the like. For example, auxins can be added to a medium at a concentration of about 0.1-about 10 ppm. Examples of the cytokinins include, but are not limited to, kinetin, benzyladenine (BA), zeatin and the like. For example, cytokinins can be added to a medium at a concentration of about 0.1-about 10 ppm.

Those of ordinary skill in the art can freely add, according to the object, sodium, potassium, calcium, magnesium, phosphorus, chlorine, various amino acids, various vitamins, antibiotic, serum, fatty acid, sugar and the like to the above-mentioned medium. For culture of animal-derived cells and/or tissues, those of ordinary skill in the art can also add, according to the object, one or more kinds of other chemical components and biogenic substances in combination. Examples of the components to be added to a medium for animal-derived cells and/or tissues include fetal bovine serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various hormones, various growth factors, various extracellular matrices, various cell adhesion molecules and the like. Examples of the cytokine to be added to a medium include, but are not limited to, interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia cell inhibitory factor (LIF), oncostatin M (OM), erythropoietin (EPO), thrombopoietin (TPO) and the like.

Examples of the hormone to be added to a medium include, but are not limited to, melatonin, serotonin, thyroxine, triiodothyronine, epinephrine, norepinephrine, dopamine, anti-mullerian hormone, adiponectin, adrenocorticotropic hormone, angiotensinogen and angiotensin, antidiuretic hormone, atrial natriuretic peptide, calcitonin, cholecystokinin, corticotropin release hormone, erythropoietin, follicle stimulating hormone, gastrin, ghrelin, glucagon, gonadotropin release hormone, growth hormone release hormone, human chorionic gonadotropin, human placental lactogen, growth hormone, inhibin, insulin, insulin-like growth factor, leptin, luteinizing hormone, melanocyte stimulating hormone, oxytocin, parathyroid hormone, prolactin, secretin, somatostatin, thrombopoietin, thyroid-stimulating hormone, thyrotropin releasing hormone, cortisol, aldosterone, testosterone, dehydroepiandrosterone, androstenedione, dihydrotestosterone, estradiol, estrone, estriol, progesterone, calcitriol, calcidiol, prostaglandin, leukotriene, prostacyclin, thromboxane, prolactin releasing hormone, lipotropin, brain natriuretic peptide, neuropeptide Y, histamine, endothelin, pancreas polypeptide, rennin and enkephalin.

Examples of the growth factor to be added to a medium include, but are not limited to, transforming growth factor-α (TGF-α), transforming growth factor-β (TGF-β), macrophage inflammatory protein-1α (MIP-1α), epithelial cell growth factor (EGF), fibroblast growth factor-1, 2, 3, 4, 5, 6, 7, 8 or 9 (FGF-1, 2, 3, 4, 5, 6, 7, 8, 9), nerve cell growth factor (NGF), hepatocyte growth factor (HGF), leukemia inhibitory factor (LIF), protease nexin I, protease nexin II, platelet-derived growth factor (PDGF), cholinergic differentiation factor (CDF), chemokine, Notch ligand (Delta1 and the like), Wnt protein, angiopoietin-like protein 2, 3, 5 or 7 (Angpt2, 3, 5, 7), insulin like growth factor (IGF), insulin-like growth factor binding protein-1 (IGFBP), Pleiotrophin and the like.

In addition, these cytokines and growth factors having amino acid sequences artificially altered by gene recombinant techniques can also be added. Examples thereof include IL-6/soluble IL-6 receptor complex, Hyper IL-6 (fusion protein of IL-6 and soluble IL-6 receptor) and the like.

Examples of the various extracellular matrices and various cell adhesion molecules include collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, matrigel, poly-D-lysine, poly-L-lysine, chitin, chitosan, sepharose, hyaluronic acid, alginate gel, various hydrogels, cleavage fragments thereof and the like.

Examples of the antibiotic to be added to a medium include sulfonamides, penicillin, phenethicillin, methicillin, oxacillin, cloxacillin, dicloxacillin, flucloxacillin, nafcillin, ampicillin, penicillin, amoxicillin, ciclacillin, carbenicillin, ticarcillin, piperacillin, azlocillin, mezlocillin, mecillinam, andinocillin, cephalosporin and a derivative thereof, oxolinic acid, amifloxacin, temafloxacin, nalidixic acid, piromidic acid, ciprofloxacin, cinoxacin, norfloxacin, perfloxacin, Rosaxacin, ofloxacin, enoxacin, pipemidic acid, sulbactam, clavulanic acid, β-bromopenisillanic acid, β-chloropenisillanic acid, 6-acetylmethylene-penisillanic acid, cephoxazole, sultampicillin, adinoshirin and sulbactam formaldehyde hudrate ester, tazobactam, aztreonam, sulfazethin, isosulfazethin, norcardicin, m-carboxyphenyl, phenylacetamidophosphonic acid methyl, chlortetracycline, oxytetracycline, tetracycline, demeclocycline, doxycycline, methacycline, and minocycline.

In a preferable embodiment, the medium (preferably, liquid medium) contains metal cations, for example, divalent metal cations (calcium ion, magnesium ion, zinc ion, iron ion and copper ion etc.), preferably calcium ion. This aims to form, upon mixing with a liquid medium, a three-dimensional network (amorphous structure) of deacylated gellan gum or a salt thereof, and an acidic polysaccharide (e.g., alginic acid) or a salt thereof capable of maintaining a random coil state in a divalent metal cation medium and cross-linking via a divalent metal ion assemble via a metal cation (e.g., divalent metal cation such as calcium ion and the like) in the liquid medium. The concentration of metal cation (preferably calcium ion) in the medium is not particularly limited as long as it is a concentration sufficient for deacylated gellan gum or a salt thereof, and an acidic polysaccharide (e.g., alginic acid) or a salt thereof capable of maintaining a random coil state in a divalent metal cation medium and cross-linking via a divalent metal ion to assemble via the metal cation and form a three-dimensional network (amorphous structure). For example, it is 0.1 mM to 300 mM, preferably 0.5 mM to 100 mM. A liquid medium containing the metal cation and deacylated gellan gum or a salt thereof, and an acidic polysaccharide (e.g., alginic acid) or a salt thereof capable of maintaining a random coil state in a divalent metal cation medium and cross-linking via a divalent metal ion may be mixed, or a medium free of the metal cation and deacylated gellan gum or a salt thereof, and an acidic polysaccharide (e.g., alginic acid) or a salt thereof capable of maintaining a random coil state in a divalent metal cation medium and cross-linking via a divalent metal ion are mixed, and thereafter, an aqueous solution of a metal cation prepared separately may be added to the mixture.

The liquid composition of the present invention may contain various components having a cell life-prolonging effect in addition to the aforementioned composition during preservation of cells and tissues in an unfrozen state. Examples of the component include, but are not limited to, saccharides (excluding polysaccharides) (e.g., monosaccharides (glucose etc.), disaccharides), antioxidant (e.g., SOD, vitamin E, glutathione, polyphenol), hydrophilic polymer (e.g., polyvinylpyrrolidone), chelating agent (e.g., EDTA), sugar alcohol (e.g., mannitol, sorbitol), glycerol and the like. In one embodiment, the liquid composition of the present invention contains at least one compound selected from the group consisting of saccharides (excluding polysaccharides) (e.g., monosaccharides (glucose etc.), disaccharides), antioxidant (e.g., SOD, vitamin E, glutathione, polyphenol), hydrophilic polymer (e.g., polyvinylpyrrolidone), chelating agent (e.g., EDTA), sugar alcohol (e.g., mannitol, sorbitol), and glycerol.

The liquid composition of the present invention containing deacylated gellan gum or a salt thereof, and an acidic polysaccharide (e.g., alginic acid) or a salt thereof capable of maintaining a random coil state in a divalent metal cation medium and cross-linking via a divalent metal ion affords an effect of maintaining good survivability of a cell or tissue preserved in an unfrozen state. Thus, it does not need to contain other components having a cell life-prolonging effect during preservation of a cell or tissue in an unfrozen state. In one embodiment, the liquid composition of the present invention does not contain at least one compound selected from the group consisting of saccharides (excluding polysaccharides) (e.g., monosaccharides (glucose etc.), disaccharides), antioxidant (e.g., SOD, vitamin E, glutathione, polyphenol), hydrophilic polymer (e.g., polyvinylpyrrolidone), chelating agent (e.g., EDTA), sugar alcohol (e.g., mannitol, sorbitol), and glycerol.

The liquid composition of the present invention does not need to contain a cryoprotectant since it is used for preservation of a cell or tissue in an unfrozen state. As the cryoprotectant, DMSO, glycerol, ethylene glycol, trimethyleneglycol, methanol, dimethylacetamide, polyethylene glycol, polyvinylpyrrolidone, hydroxyethylstarch, dextran, albumin and the like can be mentioned. In one embodiment, the liquid composition of the present invention does not contain at least one compound selected from the group consisting of DMSO, glycerol, ethylene glycol, trimethyleneglycol, methanol, dimethylacetamide, polyethylene glycol, polyvinylpyrrolidone, hydroxyethylstarch, dextran, and albumin.

When deacylated gellan gum or a salt thereof, and an acidic polysaccharide (e.g., alginic acid) or a salt thereof capable of maintaining a random coil state in a divalent metal cation medium and cross-linking via a divalent metal ion are added to the above-mentioned liquid medium, the deacylated gellan gum or a salt thereof, and the acidic polysaccharide (e.g., alginic acid) or a salt thereof capable of maintaining a random coil state in a divalent metal cation medium and cross-linking via a divalent metal ion are first dissolved or dispersed in an appropriate solvent (to be a medium additive). Thereafter, the medium additive is added to the medium such that the final concentrations of the deacylated gellan gum or a salt thereof, and the acidic polysaccharide (e.g., alginic acid) or a salt thereof capable of maintaining a random coil state in a divalent metal cation medium and cross-linking via a divalent metal ion in the liquid composition fall within the concentrations described in detail above. A medium additive containing the deacylated gellan gum or a salt thereof, and a medium additive containing the acidic polysaccharide (e.g., alginic acid) or a salt thereof capable of maintaining a random coil state in a divalent metal cation medium and cross-linking via a divalent metal ion may be prepared separately, and each may be added to the medium, or a medium additive containing both the deacylated gellan gum or a salt thereof, the acidic polysaccharide (e.g., alginic acid) or a salt thereof capable of maintaining a random coil state in a divalent metal cation medium and cross-linking via a divalent metal ion (i.e., mixture of the deacylated gellan gum or a salt thereof, and the acidic polysaccharide (e.g., alginic acid) or a salt thereof capable of maintaining a random coil state in a divalent metal cation medium and cross-linking via a divalent metal ion) may be prepared and added to the medium. Preferably, a medium additive containing both the deacylated gellan gum or a salt thereof, and the acidic polysaccharide (e.g., alginic acid) or a salt thereof capable of maintaining a random coil state in a divalent metal cation medium and cross-linking via a divalent metal ion (i.e., mixture of the deacylated gellan gum or a salt thereof, and the acidic polysaccharide (e.g., alginic acid) or a salt thereof capable of maintaining a random coil state in a divalent metal cation medium and cross-linking via a divalent metal ion) may be prepared and added to the medium.

Here, examples of an appropriate solvent used for preparation of the medium additive include, but are not limited to, hydrophilic solvents such as aqueous solvents (e.g., water, saline, PBS and the like), dimethyl sulfoxide (DMSO), various alcohols (e.g., methanol, ethanol, butanol, propanol, glycerin, propylene glycol, butyleneglycol and the like), and the like. In this case, the concentrations of deacylated gellan gum or a salt thereof, and an acidic polysaccharide (e.g., alginic acid) or a salt thereof capable of maintaining a random coil state in a divalent metal cation medium and cross-linking via a divalent metal ion in the medium additive are desirably, for example, about 10- to 500-fold, preferably about 25- to 100-fold, concentration of the final concentration of the liquid composition of the present invention described in detail above.

Deacylated gellan gum or a salt thereof, and an acidic polysaccharide (e.g., alginic acid) or a salt thereof capable of maintaining a random coil state in a divalent metal cation medium and cross-linking via a divalent metal ion may be sterilized as necessary. The sterilization method is not particularly limited, and, for example, radiation sterilization, ethylene oxide gas sterilization, high-pressure vapor sterilization (autoclave sterilization), filter sterilization and the like can be mentioned. When filter sterilization (hereinafter sometimes to be referred to as filtration sterilization) is to be performed, the material of the filter part is not particularly limited and, for example, glass fiber, nylon, PES (polyethersulfone), hydrophilic PVDF (polyvinylidene fluoride), cellulose mixed ester, celluloseacetate, polytetrafluoroethylene and the like can be mentioned. While the size of the pore in the filter is not particularly limited, it is preferably 0.1 μm to 10 μm, more preferably 0.1 μm to 1 μm, most preferably 0.1 μm to 0.5 μm. These sterilization treatments can be applied regardless of whether the deacylated gellan gum or a salt thereof, and the acidic polysaccharide (e.g., alginic acid) or a salt thereof capable of maintaining a random coil state in a divalent metal cation medium and cross-linking via a divalent metal ion are in a solid state or in a solution state.

The temperature of the high-pressure vapor sterilization treatment is generally 105-135° C., preferably 115° C.-130° C., more preferably 118-123° C. (e.g., 121±1° C.). The pressure in the sterilization treatment is generally 0.12-0.32 MPa, preferably 0.17-0.27 MPa, more preferably 0.19-0.23 MPa (e.g., 0.21±0.1 MPa). The sterilization treatment time is generally 1-60 min, preferably 5-45 min, more preferably 15-25 min (e.g., 20±1 min).

The combination of the high-pressure vapor sterilization treatment conditions is, for example, 105-135° C., 0.12-0.32 MPa, 1-60 min; preferably 115° C.-130° C., 0.17-0.27 MPa, 5-45 min; more preferably 118-123° C. (e.g., 121±1° C.), 0.19-0.23 MPa (e.g., 0.21±0.1 MPa), 15-25 min (e.g., 20±1 min).

By adding a solution or dispersion of deacylated gellan gum or a salt thereof and an acidic polysaccharide (e.g., alginic acid) or a salt thereof capable of maintaining a random coil state in a divalent metal cation medium and cross-linking via a divalent metal ion to a liquid medium, the deacylated gellan gum or a salt thereof, and the acidic polysaccharide (e.g., alginic acid) or a salt thereof capable of maintaining a random coil state in a divalent metal cation medium and cross-linking via a divalent metal ion assemble via a metal cation (e.g., divalent metal cation such as calcium ion and the like) in the liquid medium, whereby a three-dimensional network (amorphous structure) is formed and the liquid composition of the present invention can be obtained. Media generally contain a metal cation (e.g., calcium ion) at a concentration sufficient to produce an assembly of deacylated gellan gum or a salt thereof, and an acidic polysaccharide (e.g., alginic acid) or a salt thereof capable of maintaining a random coil state in a divalent metal cation medium and cross-linking via a divalent metal ion to form a three-dimensional network (amorphous structure). Thus, the liquid composition of the present invention can be obtained by simply adding, to a liquid medium, a solution or dispersion of deacylated gellan gum or a salt thereof and an acidic polysaccharide (e.g., alginic acid) or a salt thereof capable of maintaining a random coil state in a divalent metal cation medium and cross-linking via a divalent metal ion. Alternatively, a medium may be added to the medium additive (solution or dispersion of deacylated gellan gum or a salt thereof, and an acidic polysaccharide (e.g., alginic acid) or a salt thereof capable of maintaining a random coil state in a divalent metal cation medium and cross-linking via a divalent metal ion) of the present invention. Furthermore, the liquid composition of the present invention can also be prepared by mixing deacylated gellan gum or a salt thereof, and an acidic polysaccharide (e.g., alginic acid) or a salt thereof capable of maintaining a random coil state in a divalent metal cation medium and cross-linking via a divalent metal ion and a medium component (a powder medium or concentrated medium) in an aqueous solvent (e.g., water including ion exchanged water, ultrapure water and the like). Examples of the embodiment of mixing include, but are not limited to, (1) mixing a liquid medium and a medium additive (solution), (2) adding a solid (powder etc.) of deacylated gellan gum or a salt thereof, and an acidic polysaccharide (e.g., alginic acid) or a salt thereof capable of maintaining a random coil state in a divalent metal cation medium and cross-linking via a divalent metal ion to a liquid medium, (3) mixing a medium additive (solution) and a powder medium, (4) mixing powder medium and a solid (powder etc.) of deacylated gellan gum or a salt thereof, and an acidic polysaccharide (e.g., alginic acid) or a salt thereof capable of maintaining a random coil state in a divalent metal cation medium and cross-linking via a divalent metal ion with an aqueous solvent, and the like. To prevent distribution of deacylated gellan gum or a salt thereof, and an acidic polysaccharide (e.g., alginic acid) or a salt thereof capable of maintaining a random coil state in a divalent metal cation medium and cross-linking via a divalent metal ion in a liquid composition from being non-uniform, the embodiment of (1) is preferable.

When deacylated gellan gum or a salt thereof and an acidic polysaccharide (e.g., alginic acid) or a salt thereof capable of maintaining a random coil state in a divalent metal cation medium and cross-linking via a divalent metal ion are dissolved in a solvent (e.g., aqueous solvent such as water, liquid medium and the like), or deacylated gellan gum or a salt thereof, and an acidic polysaccharide (e.g., alginic acid) or a salt thereof capable of maintaining a random coil state in a divalent metal cation medium and cross-linking via a divalent metal ion, and a powder medium are dissolved in a solvent, the mixture may be heated to promote dissolution. Examples of the heat temperature include 80° C.-130° C., preferably 100° C.-125° C. (e.g., 121° C.) at which heating sterilization is performed. After heating, the obtained solution of the deacylated gellan gum or a salt thereof and the acidic polysaccharide (e.g., alginic acid) or a salt thereof capable of maintaining a random coil state in a divalent metal cation medium and cross-linking via a divalent metal ion is cooled to room temperature. By adding the aforementioned metal cations (e.g., divalent metal cations such as calcium ion and the like) to the solution (e.g., adding the solution to liquid medium), the deacylated gellan gum or a salt thereof, and the acidic polysaccharide (e.g., alginic acid) or a salt thereof capable of maintaining a random coil state in a divalent metal cation medium and cross-linking via a divalent metal ion assemble via a metal cation (e.g., divalent metal cation such as calcium ion and the like), thus forming a three-dimensional network (amorphous structure), and the liquid composition of the present invention can be obtained. Alternatively, a three-dimensional network (amorphous structure) can also be formed by dissolving deacylated gellan gum or a salt thereof, and an acidic polysaccharide (e.g., alginic acid) or a salt thereof capable of maintaining a random coil state in a divalent metal cation medium and cross-linking via a divalent metal ion in a solvent (e.g., aqueous solvent such as water, liquid medium and the like) containing the aforementioned metal cations (e.g., divalent metal cations such as calcium ion and the like) with heating (e.g., 80° C.130° C., preferably 100° C.-125° C. (e.g., 121° C.)), and cooling the obtained solution to room temperature, since an assembly of the deacylated gellan gum or a salt thereof, and the acidic polysaccharide (e.g., alginic acid) or a salt thereof capable of maintaining a random coil state in a divalent metal cation medium and cross-linking via a divalent metal ion via a metal cation (e.g., divalent metal cation such as calcium ion and the like) occurs.

Deacylated gellan gum or a salt thereof has a constituent unit having a comparatively linear structure and plural sugar chains are bundled when added to a solvent (e.g., water) and is not dissolved easily. However, when an acidic polysaccharide (e.g., alginic acid) or a salt thereof capable of maintaining a random coil state in a divalent metal cation medium and cross-linking via a divalent metal ion is added, bundling of deacylated gellan gum or a salt thereof is suppressed due to the comparatively bulky structure involving both uronic acids of α1-4 bonded L-glucuronic acid and β1-4 bonded D-mannuronic acid, and deacylated gellan gum or a salt thereof is dissolved comparatively easily. Therefore, deacylated gellan gum or a salt thereof and an acidic polysaccharide (e.g., alginic acid) or a salt thereof capable of maintaining a random coil state in a divalent metal cation medium and cross-linking via a divalent metal ion can be dissolved in a solvent (e.g., aqueous solvent such as water, liquid medium and the like) at a comparatively low temperature (e.g., 0-37° C., preferably, 10-30° C.) without heating.

Examples of the production method of the liquid composition of the present invention are shown below, which are not to be construed as limitative.

Deacylated gellan gum or a salt thereof, and an acidic polysaccharide (e.g., alginic acid) or a salt thereof capable of maintaining a random coil state in a divalent metal cation medium and cross-linking via a divalent metal ion are added to ion exchange water or ultrapure water. Then, they are stirred at a temperature at which the deacylated gellan gum or a salt thereof and the acidic polysaccharide (e.g., alginic acid) or a salt thereof capable of maintaining a random coil state in a divalent metal cation medium and cross-linking via a divalent metal ion can be dissolved (e.g., 5-60° C., preferably 5-40° C., more preferably 10-30° C.) to allow for dissolution to a transparent state.

After dissolving, the mixture is allowed to cool with stirring as necessary, and sterilized (e.g., autoclave sterilization at 121° C. for 20 min, filter filtration). The aforementioned sterilized aqueous solution is added with stirring (e.g., homomixer etc.) to a given medium to uniformly mix the solution with the medium. The mixing method of the aqueous solution and the medium is not particularly limited, and may be manual mixing such as pipetting etc., or mixing with an instrument such as magnetic stirrer, mechanical stirrer, homomixer and homogenizer.

For uniform dispersing of deacylated gellan gum or a salt thereof and an acidic polysaccharide (e.g., alginic acid) or a salt thereof capable of maintaining a random coil state in a divalent metal cation medium and cross-linking via a divalent metal ion in a liquid medium, for example, the liquid medium is placed in a conical tube, stirring is maintained by vortex and the like, and an aqueous solution of the deacylated gellan gum or a salt thereof and the acidic polysaccharide (e.g., alginic acid) or a salt thereof capable of maintaining a random coil state in a divalent metal cation medium and cross-linking via a divalent metal ion may be vigorously flushed into the liquid medium with a syringe with a syringe needle. Using a medium preparation kit (Nissan Chemical Industries FCeM™-series Preparation Kit), the liquid composition of the present invention in which a three-dimensional network (amorphous structure) formed by an assembly of deacylated gellan gum or a salt thereof, and an acidic polysaccharide (e.g., alginic acid) or a salt thereof capable of maintaining a random coil state in a divalent metal cation medium and cross-linking via a divalent metal ion via a metal cation (e.g., divalent metal cation such as calcium ion and the like) is uniformly dispersed can be prepared with ease.

The liquid composition of the present invention may be filtrated through a filter after mixing. The size of the pore of the filter to be used for the filtration treatment is 5 µm to 100 µm, preferably 5 µm to 70 µm, more preferably 10 µm to 70 µm.

Preservation Method of Cell or Tissue

The present invention also provides a method for preserving cells or tissues including preserving the cells or tissues in an unfrozen state in the above-mentioned liquid composition of the present invention. In a preferable embodiment, the preservation method of the present invention can preserve or transport a cell or tissue in a suspended state (preferably, in a static suspended state) in the liquid composition of the present invention.

As the cells and tissues to be preserved in the liquid composition of the present invention, those described in detail in the aforementioned [liquid composition] can be mentioned.

The form and state of the cells and tissues to be preserved by the method of the present invention can be freely selected by those of ordinary skill in the art. Specific examples of the state of the cells to be preserved include, but are not limited to, a state in which the cells are dispersed in a single cell, a state in which the cells adhere to a carrier surface, a state in which the cells are embedded inside a carrier, a state in which a plurality of cells are aggregated to form a cell mass (e.g., sphere), a state in which two or more kinds of cells are aggregated to form a cell mass (e.g., sphere) and the like. Among these states, the state in which a cell mass (e.g., sphere) is formed can be recited as the most preferable state to be preserved by the method of the present invention because cell-cell interactions and cell structure close to those in the in-vivo environment are reconstructed, it can be preserved while maintaining cell functions for a long term, and collection of cells is relatively easy. The cell mass is preferably a sphere containing mammalian stem cells (e.g., embryonic stem cells (ES cell), embryonal carcinoma cell, embryonic germ cell, induced pluripotent stem cell (iPS cell), neural stem cell, hematopoietic stem cell, mesenchymal stem cell, liver stem cell, pancreatic stem cell, muscle stem cell, germ stem cell, intestinal stem cell, cancer stem cell, hair follicle stem cell, cancer stem cell) or progenitor cell. Examples of the sphere in the present invention include aggregates form by some tens to some hundreds of cells. Sphere can be produced by a known method.

When cells are preserved in the liquid composition of the present invention, the cell concentration is not particularly limited as long as the cells can be preserved in an unfrozen state while maintaining good survivability. It is typically $0.1\times10^4$-$200\times10^4$ cells/ml, preferably $1\times10^4$-$100\times10^4$ cells/ml.

In the preservation method of the present invention, the desired cell or tissue is dispersed in the liquid composition of the present invention and placed in a sealable container. Examples of the container include, but are not limited to, flask, plastic bag, Teflon (registered trade mark) bag, tube, culture bag and the like. To avoid leakage of contents and contamination with bacteria and the like from the outside world during preservation, the container in which a dispersion of the cell or tissue in the liquid composition of the present invention is preferably sealed.

As mentioned above, in the liquid composition of the present invention, a three-dimensional network (amorphous structure) is formed by deacylated gellan gum or a salt thereof, and an acidic polysaccharide (e.g., alginic acid) or a salt thereof capable of maintaining a random coil state in a divalent metal cation medium and cross-linking via a divalent metal ion, which are assembled via a metal cation (e.g., divalent metal cation such as calcium ion and the like). When a cell or tissue is preserved in the liquid composition of the present invention, the cell or tissue suspended in the liquid composition is trapped in the three-dimensional network and does not form a sediment, which in turn enables preservation of the cell or tissue under uniform dispersion in a suspended state (static suspension preservation). On the other hand, the three-dimensional network containing an acidic polysaccharide (e.g., alginic acid) or a salt thereof capable of maintaining a random coil state in a divalent metal cation medium and cross-linking via a divalent metal ion is fragile to a shear force. When a chelating agent is added as necessary to the liquid composition of the present invention, or a preserved preparation containing the cell or tissue, and a shear force sufficient to break the three-dimensional network is applied by pipetting or the like, the property of suspending cells or tissues based on the three-dimensional network is quickly lost. Therefore, it is possible to uniformly disperse and suspend cells and tissues quickly in the liquid composition of the present invention by breaking a three-dimensional network (amorphous structure)

formed by an assembly of deacylated gellan gum or a salt thereof, and an acidic polysaccharide (e.g., alginic acid) or a salt thereof capable of maintaining a random coil state in a divalent metal cation medium and cross-linking via a divalent metal ion via a metal cation (e.g., divalent metal cation such as calcium ion and the like) by a shear force such as pipetting, stirring and the like at the start of preservation. Importantly, destruction of the three-dimensional network (amorphous structure) by the shear force (loss of the effect of maintaining the suspended state of the cells or tissues by a shear force) is a reversible reaction, and when a suspension of the obtained cells and tissues is left standing, the fragments of the destroyed three-dimensional network (amorphous structure) assemble again via a metal cation (e.g., divalent metal cation such as calcium ion and the like) and regenerate a three-dimensional network (amorphous structure) to show again the property of maintaining the suspended state of the cells or tissues, and cells and tissues can be preserved while maintaining a suspended state.

The temperature during preservation is not particularly limited as long as survival of the cell or tissue is maintained. It is typically not more than 37° C. A lower temperature can avoid a decrease in the survivability of the cells or tissues during preservation. The cells or tissues are typically preserved at a temperature above the melting point of the liquid composition of the present invention so that they will not freeze. Therefore, the temperature during preservation is typically maintained at 0-37° C., preferably 1-30° C., more preferably 15-30° C. (e.g., ordinary temperature m preservation at 15-25° C.), further preferably 22-28° C., furthermore preferably 24-26° C. (e.g., 25° C.).

To enable preservation of cells or tissues in a static suspended state, the temperature during preservation is preferably a temperature at which the liquid composition of the present invention enables static suspension of cells or tissues to be preserved.

The period of preservation is not particularly limited as long as the survival state of the cells or tissues to be preserved in the liquid composition of the present invention can be maintained. It is typically not less than 1 hr (e.g., not less than 12 hr, not less than 24 hr (one day), not less than two days). The upper limit of the preservation period is not particularly limited as long as the survival state of the cells or tissues to be preserved in the liquid composition of the present invention can be maintained. It is typically within 28 days (e.g., within 21 days, within 14 days, within 7 days, within 3 days). The preservation period is appropriately determined according to the object to be preserved. During storage or transportation, the cells or tissues are preferably maintained in a static suspended state in the liquid composition of the present invention.

In one embodiment, cells or tissues are preserved in the liquid composition of the present invention under an environment accompanying vibration. As the "environment accompanying vibration", during transportation of cells or tissues can be mentioned. That is, the preservation method of the present invention can also be considered as a method for transporting cells or tissues in the liquid composition of the present invention while preserving the cells or tissues in an unfrozen state.

Using the preservation method of the present invention, cells or tissues can be maintained in a suspended state. Thus, detachment from plates due to vibration during transportation, and damage on cells and tissues due to coagulation of the cells and tissues brought into contact with each other by sedimentation can be avoided and cells or tissues can be preserved while maintaining the original functions. When spheres are preserved by the method of the present invention, the spheres can be maintained in a suspended state. Thus, vibration during transportation and coagulation of the spheres due to vibration can be avoided, and the spheres can be preserved while maintaining the form of the spheres.

Recovery of Preserved Cells or Tissues

The present invention also provides a method for efficiently recovering a cell or tissue from a preserved preparation obtained by preserving cells or tissues in the liquid composition of the present invention. The recovery method of the present invention characteristically applies a shear force to the preserved preparation.

As mentioned above, a three-dimensional network (amorphous structure) is formed by an assembly of deacylated gellan gum or a salt thereof, and an acidic polysaccharide (e.g., alginic acid) or a salt thereof capable of maintaining a random coil state in a divalent metal cation medium and cross-linking via a divalent metal ion via a metal cation (e.g., divalent metal cation such as calcium ion and the like) in the liquid composition of the present invention. When cells or tissues are preserved in the liquid composition of the present invention, the cells or tissues suspended in the liquid composition are trapped in the three-dimensional network and do not form sediments. Therefore, the cells or tissues can be preserved while being uniformly dispersed in a suspended state (static suspension culture). On the other hand, the three-dimensional network containing an acidic polysaccharide (e.g., alginic acid) or a salt thereof capable of maintaining a random coil state in a divalent metal cation medium and cross-linking via a divalent metal ion is fragile to a shear force and, when a chelating agent is added as necessary to a preserved preparation containing the liquid composition of the present invention, and the cells or tissues, and a shear force sufficient to destroy the three-dimensional network is applied thereto, the property to suspend cells or tissues based on the three-dimensional network is rapidly lost, and the cells or tissues easily form sediments due to gravity. When the preserved preparation in this state is centrifuged, the cells or tissues contained therein easily form sediments, and the cells or tissues can be recovered by removing the liquid composition in the supernatant.

The operation to apply a shear force to a preserved preparation is not particularly limited as long as a three-dimensional network (amorphous structure) formed by an assembly of deacylated gellan gum or a salt thereof, and an acidic polysaccharide (e.g., alginic acid) or a salt thereof capable of maintaining a random coil state in a divalent metal cation medium and cross-linking via a divalent metal ion via a metal cation (e.g., divalent metal cation such as calcium ion and the like) can be destroyed. For example, pipetting, filter filtration, stirring, ultrasonication and the like can be mentioned.

To apply a sufficient shear force to the preserved preparation, pipetting is preferably performed using a pipette with a comparatively narrow tip (inner diameter of tip is, for example, not more than 5 mm, preferably 0.1-3.0 mm, more preferably 0.5-2.0 mm).

To rapidly stir the preserved preparation as a whole, it is preferable to suck and discharge, for example, not less than 1%, preferably not less than 10%, more preferably not less than 20%, further preferably not less than 30%, further more preferably not less than 50%, of the volume of the preserved preparation by one operation.

To apply a sufficient shear force to the preserved preparation, for example, it is preferable to perform a sucking and/or discharging operation at a flow rate of not less than 1 ml/sec, preferably 2-20 ml/sec, more preferably 5-10 ml/sec.

The number of times of pipetting is not particularly limited as long as it is sufficient to destroy the above-mentioned three-dimensional network. Generally, pipetting is continuously performed not less than one time, preferably not less than 3 times, more preferably not less than 5 times. The more the number of times of pipetting is, the more certainly the above-mentioned three-dimensional network is destroyed and a higher number is preferable. There is no theoretical upper limit thereof. However, when the number of times of pipetting is too many, the survival rate of the cells or tissues decreases. Thus, the number is preferably set to generally not more than 50, preferably not more than 20, more preferably not more than 15. The number of times of pipetting is generally 1-50, preferably 3-20, more preferably 5-15.

The size of the fine pores in the filter (pore size) is not particularly limited as long as it is within the range capable of destroying the above-mentioned three-dimensional network. It is generally not more than 500 μm, preferably not more than 200 μm, more preferably not more than 100 μm. The smaller the pore size is, the more strongly the shear force acts on the preserved preparation, and the more certainly the above-mentioned three-dimensional network is destroyed. When it is too small, the preservation composition cannot pass through the filter with ease. Thus, the size of the fine pores in the filter (pore size) is generally not less than 5 μm, preferably not less than 10 μm, more preferably not less than 20 μm, further preferably not less than 40 μm.

The pore diameter of the filter is preferably one that permits cells or tissues in the preserved preparation to pass through. Here, the "size that permits cells or tissues to pass through" means a size that allows passage of cells or tissues while maintaining survival. For example, the "size that permits cells or tissues to pass through" encompasses not only when the pore diameter of the filter is larger than the diameter of the cells or tissues to be preserved but also an embodiment in which a cell mass (e.g., sphere) or tissue in the preserved preparation passes through a filter having a pore diameter smaller than the diameter thereof, whereby it is divided into multiple cells, cell masses (e.g., spheres) or tissues while maintaining survival. While the size of the cell cannot be defined unconditionally since it depends on the kind of the cell, since a general cell having a diameter of about 7.5-20 μm can easily pass through a filter having a pore diameter of not less than 20 μm, preferably 40 μm, in a single cell state while maintaining good survivability. Therefore, to efficiently destroy the above-mentioned three-dimensional network while maintaining good survivability of the cells or tissues, the pore size of the filter is, for example, 20-200 μm, preferably 40-100 μm.

Examples of the material of the filter include, but are not particularly limited to, polyethylene, polypropylene, polyamide (nylon), polysulphone, polypropylene, acryl, polylactic acid, cellulose mixed ester, polycarbonate, polyester, glass and the like. While the properties such as polarity, chargeability, hydrophilicity and the like vary depending on the material, the correlation between these properties and the recovery rate is weak, and a good recovery rate is expected irrespective of the material used. Polyamide (nylon), polyethylene, polyester, glass and the like are preferable from the aspects of easy availability and the like.

As these filters, commercially available products may be used, and concrete examples thereof include CellTrics filter (trade mark) manufactured by Partec: pore diameter 5 μm (model number 06-04-004-2323), 10 μm (model number 06-04-004-2324), 20 μm (model number 06-04-004-2325), 30 μm (model number 06-04-004-2326), 50 μm (model number 06-04-004-2327), 100 μm (model number 06-04-004-2328) and 150 μm (model number 06-04-004-2329), Cell Strainer (trade mark) manufactured by Becton, Dickinson and Company: pore diameter 40 μm (model number 352340), 70 μm (model number 352350) and 100 μm (model number 352360), Filcon S (trade mark) manufactured by AS ONE: pore diameter 20 μm (model number 2-7211-01), 30 μm (model number 2-7211-02), 50 μm (model number 2-7211-03), 70 μm (model number 2-7211-04), 100 μm (model number 2-7211-05) and 200 μm (model number 2-7211-06) and the like.

While the number of passages through the filter may be one, it is possible to improve the recovery rate of cells or tissues by passing them through the filter multiple times as necessary. The number of passages through the filter is generally 1-10.

For passing through a filter multiple times, an operation including passing a preserved preparation of cells or tissues through a single filter and collecting the passed suspension may be carried out a plurality of times, or a preserved preparation of cells or tissues may be passed through a multiple filter containing a plurality of filter membranes (e.g., 3-5 filter membranes) layered together. The use of a multiple layered filter is advantageous from the viewpoint of operation efficiency. For passage through a filter multiple times, a plurality of filters having the same pore diameter may be used, or a plurality of filters having different pore diameters may be used in combination. Preferably, a plurality of filters (e.g., 3-5 filters) having the same pore diameter (e.g., 40-100 μm) are stacked and used.

Examples of the stirring operation include vortex, mixing by inverting, magnetic stirrer, paddle and the like. The speed of vortex is, for example, 200-3,000 rpm.

When a shear force is applied to a preserved preparation, a chelating agent may be added as necessary to the culture preparation. By adding a chelating agent, a metal cation (preferably divalent metal cations such as calcium ion, magnesium ion and the like) is removed from the above-mentioned three-dimensional network contained in the liquid composition, and the binding of polysaccharides (deacylated gellan gum or a salt thereof, and an acidic polysaccharide (e.g., alginic acid) or a salt thereof capable of maintaining a random coil state in a divalent metal cation medium and cross-linking via a divalent metal ion) with each other via the metal cation in the three-dimensional network becomes loose and the three-dimensional network is partially destroyed, whereby the recovery rate of the cells or tissues is expected to be improved.

While the chelating agent is not particularly limited as long as it is a compound capable of forming a complex with a divalent metal cation such as calcium ion, magnesium ion and the like (preferably, calcium ion). Examples thereof include citric acid or a salt thereof (e.g., trisodium citrate); EDTA or a salt thereof (e.g., sodium edetates such as EDTA2Na, EDTA3Na, EDTA4Na and the like); salts of hydroxyethylethylenediamine triacetic acid such as HEDTA3Na and the like; EGTA or a salt thereof; pentetate (salts of diethylenetriamine pentaacetic acid); phytic acid; phosphonic acid such as etidronic acid and the like and salts thereof including sodium salt; sodium oxalate; polyamino acids such as polyaspartic acid, polyglutamic acid and the like; sodium polyphosphate; sodium metaphosphate; phosphoric acid; alanine; dihydroxyethylglycine; gluconic acid; ascorbic acid; succinic acid; tartaric acid and the like. To improve recovery rates of cells or tissues, citric acid or a salt thereof (e.g., trisodium citrate) or EDTA or a salt thereof (e.g., sodium edetates such as EDTA2Na, EDTA3Na, EDTA4Na and the like) is preferable. Two or more kinds of the chelating agents can also be used in a mixture. While the combination of chelating agent is not particularly limited, for example, a combination of citric acid or a salt thereof (e.g., trisodium citrate) and EDTA or a salt thereof (e.g., sodium edetates such as EDTA2Na, EDTA3Na, EDTA4Na and the like) can be mentioned.

The amount of a chelating agent to be added is an amount capable of loosening the binding of polysaccharides (deacylated gellan gum or a salt thereof, and an acidic polysaccharide (e.g., alginic acid) or a salt thereof capable of maintaining a random coil state in a divalent metal cation medium and cross-linking via a divalent metal ion) with each other via the metal cation in the above-mentioned three-dimensional network contained in the liquid composition of the present invention.

For example, in the case of citric acid or a salt thereof (e.g., trisodium citrate), it is generally not less than 0.001 w/v %, preferably, not less than 0.005 w/v %, as the final concentration immediately after addition. Theoretically, the upper limit is a saturated concentration of citric acid or a salt thereof. When the concentration is too high, an influence on the survival of cells or tissues is feared. Therefore, it is generally not more than 0.2 w/v %, more preferably not more than 0.1 w/v %.

In the case of EDTA or a salt (e.g., sodium edetates such as EDTA2Na, EDTA3Na, EDTA4Na and the like), generally, the final concentration immediately after addition is not less than 0.001 w/v %, preferably not less than 0.005 w/v %. Theoretically, the upper limit is a saturated concentration of EDTA or a salt thereof. When the concentration is too high, an influence on the survival of cells or tissues is feared. Therefore, it is generally not more than 0.2 w/v %, more preferably not more than 0.1 w/v %.

After addition of the chelating agent to the aforementioned preserved preparation, the obtained mixture is preferably stirred well by an operation to apply a shear force to the aforementioned preserved preparation so that the chelating agent will be uniform.

After the aforementioned pre-treatment step, the resultant mixture containing cells or tissues is subjected to centrifugation to precipitate the cells or tissues and fractions other than the cells or tissues (e.g., the liquid composition of the present invention in the supernatant) are removed, whereby the cells and/or tissues can be finally recovered from the preserved preparation of the cells or tissues. Techniques for precipitating cells or tissues by centrifugation are well known to those of ordinary skill in the art and appropriate conditions can be set by those of ordinary skill in the art according to the type of cell or tissue. In general, cells or tissues can be precipitated and separated from the supernatant by centrifugation with a centrifugal force of about 10-400 G.

As mentioned above, the loss of the effect of maintaining the suspended state of the cells or tissues by a shear force by pipetting, filter filtration and the like is a reversible reaction. Therefore, it is preferable to perform centrifugation after the above-mentioned pre-treatment step and before regeneration of the three-dimensional network (amorphous structure). For example, centrifugation is started within 60 min, preferably 30 min, more preferably 10 min, after completion of the above-mentioned pre-treatment step.

The present invention is explained in more detail in the following by concretely describing Examples of the liquid composition of the present invention, which are not to be construed as limitative.

EXAMPLE

Experimental Example 1

Production of Polysaccharide Mixture 1 part by mass of sodium alginate (ALG) (KIMICA ALGIN IL-2, manufactured by KIMICA Corporation) and 99 parts by mass of purified water were added to a glass medium bottle, and the mixture was subjected to an autoclave sterilization treatment (121° C., 20 min) to give 1 mass % concentration of an aqueous ALG solution.

In the same manner, 1 mass % concentration of aqueous deacylated gellan gum (DAG) (KELCOGEL CG-LA, manufactured by SANSHO Co., Ltd.) solutions were produced.

The aqueous ALG solution and aqueous DAG solution were fractionated at a ratio of 2:1 (v/v) into conical tubes and carefully mixed by pipetting and homogenized using a disposable syringe with a syringe needle to give a polysaccharide mixture.

Experimental Example 2

Production of Liquid Composition

The liquid composition of the present invention was produced using a medium production kit (Nissan Chemical Industries, FCeM™-series Preparation Kit). Given amounts of various media were dispensed to conical tubes (SUMITOMO BAKELITE CO., LTD. 50 mL centrifuge tube) and an adapter cap, which was a constitution of the kit, was set. The tip of a disposable syringe filled with a given amount of a polysaccharide mixture obtained in Experimental Example 1 was fitted into the cylindrical portion of the adapter cap to establish connection. The plunger of the syringe was pushed manually to vigorously inject the polysaccharide mixture in the syringe into the container, thus allowing instantaneous mixing with the medium, whereby the liquid compositions of the present invention were produced. The produced liquid compositions are shown in Table 1.

TABLE 1

| | medium | | 1% polysaccharide mixture | | prepared medium polysaccharide final |
|---|---|---|---|---|---|
| No. | kind | amount [mL] | polysaccharide composition | amount added [mL] | concentration [%] |
| Comparative Example 1 | Leibovitz's L-15/10% FBS | 50 | — | — | 0 |
| DHb084 | Leibovitz's L-15/10% FBS | 50 | ALG/DAG 2:1 (w/w) | 0.51 | 0.010 |
| DHb085 | Leibovitz's L-15/10% FBS | 50 | ALG/DAG 2:1 (w/w) | 0.66 | 0.013 |
| DHb086 | Leibovitz's L-15/10% FBS | 49.2 | ALG/DAG 2:1 (w/w) | 0.8 | 0.016 |

TABLE 1-continued

| No. | medium kind | medium amount [mL] | 1% polysaccharide mixture polysaccharide composition | amount added [mL] | prepared medium polysaccharide final concentration [%] |
|---|---|---|---|---|---|
| DHb087 | Leibovitz's L-15/10% FBS | 49 | ALG/DAG 2:1 (w/w) | 1.0 | 0.020 |
| Comparative Example 2 | DMEM-Low Glucose/10% FBS | 50 | — | — | 0 |
| DHb090 | DMEM-Low Glucose/10% FBS | 49.2 | ALG/DAG 2:1 (w/w) | 0.8 | 0.016 |

[Analysis] Measurement of Viscosity of Liquid Composition

The viscosity of the liquid composition prepared in Experimental Example 2 was measured. As a representative example, DHb087 was measured using an E-type viscometer (manufactured by TOKI SANGYO CO., LTD., Viscometer TVE-22L, standard rotor 1° 34'xR24) under 25° C. conditions at rotating speed 100 rpm for 5 min. As a result, the mean of the values measured three times was 2.07 mPa·s (first time 1.95 mPa·s, second time 2.21 mPa·s, third time 2.05 mPa·s).

Experimental Example 3

Cell Preservation (Cell Type: NHDF)

Cell suspensions containing normal human neonatal foreskin skin fibroblasts (NHDF, KURABO INDUSTRIES LTD.) ($152 \times 10^4$ cells) were prepared and dispensed into four conical tubes by $38 \times 10^4$ cells. After centrifugation (300× g, 3 min), the supernatant was removed, and liquid compositions containing DAG and ALG (total concentration 0.016 (w/v) %) (DHb086 to DHb090) or liquid compositions free of DAG or ALG (Comparative Example 1 and Comparative Example 2) (1.9 mL) for comparison, which are shown in Table 1, were added and resuspended therein, whereby cell suspensions ($20 \times 10^4$ cells/mL) containing each liquid composition were produced. These were dispensed into 1.5 mL round-bottom micro tubes (18 tubes) by 100 μL each, lid was closed and the suspension was preserved by standing at $25(\pm 1)°$ C. Three tubes each were taken out on the day of the start of preservation, days 1, 4, 7, 14, and 21 of preservation, and the amount of ATP contained in the cells was quantified by a plate reader (infiniteM200PRO manufactured by Tecan Japan Co., Ltd.) and using CellTiter-Glo reagent (manufactured by Promega Corporation). With the RLU value obtained by measuring on the day of the start of preservation as the standard (cell survival rate 100%), the RLU values obtained by measuring after preservation for each number of days were compared, and the cell survival rate after the lapse of time was calculated, based on which the cell preservability was evaluated. The mean of 3 measurements by the above-mentioned test is shown in Table 2.

TABLE 2

| preserved medium | | Comparative Example 1 | DHb086 | Comparative Example 2 | DHb090 |
|---|---|---|---|---|---|
| concentration (%) of polysaccharide in medium | | 0 | 0.016 | 0 | 0.016 |
| cell survival rate (%) | date of start | 100 | 100 | 100 | 100 |
| | day 1 | 88.7 | 104.1 | 76.8 | 78.4 |
| | day 4 | 75.7 | 88.9 | 25.1 | 50.0 |
| | day 7 | 75.4 | 90.9 | 6.0 | 18.0 |
| | day 14 | 56.0 | 83.0 | — | — |
| | day 21 | 30.3 | 74.4 | — | — |

From Table 2, the survival rate decreased to 30% in Comparative Example 1 without containing a polysaccharide composition, whereas about 70% of DHb086 which is a liquid composition containing DAG and ALG survived even after 3 weeks, and 50% survival was confirmed 4 days later in DHb090. From this, it was confirmed that a liquid composition containing DAG and ALG exhibits a cell preserving effect.

Experimental Example 4

Cell Preservation (Cell Type: NHDF)

Cell suspensions containing normal human neonatal foreskin skin fibroblasts (NHDF, KURABO INDUSTRIES LTD.) ($310 \times 10^4$ cells) were prepared and dispensed into five conical tubes by $62 \times 10^4$ cells. After centrifugation (300× g, 3 min), the supernatant was removed, and liquid compositions containing DAG and ALG (total concentration 0.010, 0.013, 0.016, 0.020 (w/v) %) (Table 1 DHb084, DHb085, DHb086, or DHb087) or a liquid composition free of DAG or ALG (Comparative Example 1) (3.1 mL) for comparison, which are shown in Table 1, were added and resuspended therein, whereby cell suspensions ($20 \times 10^4$ cells/mL) containing each liquid composition were produced. These were dispensed into 5 wells each of six 96-well U-bottom cell culture plates (manufactured by SUMITOMO BAKELITE CO., LTD., MS-309UR) by 100 μL per 1 well, covered with a lid and preserved by standing at $25(\pm 1)°$ C. The amount of ATP contained in the cells of 5 wells was quantified on the day of the start of preservation, days 1, 3, 7, 14, and 21 of preservation by a plate reader (infiniteM200PRO manufactured by Tecan Japan Co., Ltd.) and using CellTiter-Glo reagent (manufactured by Promega Corporation). With the RLU value obtained by measuring on the day of the start of preservation as the standard (cell survival rate 100%), the RLU values obtained by measuring after preservation for each number of days were compared, and the cell survival rate after the lapse of time was calculated, based on which the cell preservability was evaluated. The mean of 5 measurements by the above-mentioned test is shown in Table 3.

TABLE 3

| preserved medium | | Comparative Example 1 | DHb084 | DHb085 | DHb086 | DHb087 |
|---|---|---|---|---|---|---|
| concentration (%) of polysaccharide in medium | | 0 | 0.010 | 0.013 | 0.016 | 0.020 |
| cell survival rate (%) | date of start | 100 | 100 | 100 | 100 | 100 |
| | day 1 | 107.9 | 109.7 | 106.4 | 108.6 | 104.0 |
| | day 3 | 81.6 | 82.7 | 82.9 | 83.6 | 84.6 |
| | day 7 | 70.3 | 87.4 | 85.6 | 86.6 | 82.9 |
| | day 14 | 53.3 | 76.8 | 74.3 | 75.8 | 68.8 |
| | day 21 | 49.2 | 75.6 | 75.2 | 78.0 | 71.9 |

From Table 3, all polysaccharide concentrations showed a survival rate of not less than about 70% in 3 weeks, and a high cell preserving effect of the liquid compositions containing DAG and ALG was confirmed.

Experimental Example 5

Cell Preservation (Cell Type: h-MSC)

Cell suspensions containing human bone marrow-derived mesenchymal stem cells (h-MSC, manufactured by LONZA) ($104 \times 10^4$ cells) were prepared and dispensed into four conical tubes by $26 \times 10^4$ cells. After centrifugation ($300 \times$ g, 3 min), the supernatant was removed, and liquid compositions containing DAG and ALG (total concentration 0.016 (w/v) %) (Example DHb086 to DHb090) or liquid compositions free of DAG or ALG (Comparative Example 1 and Comparative Example 2) (1.3 mL) for comparison, which are shown in Table 1, were added and resuspended therein, whereby cell suspensions ($20 \times 10^4$ cells/mL) containing each liquid composition were produced. These were dispensed into 1.5 mL round-bottom micro tubes (12 tubes) by 100 μL each, lid was closed and the suspension was preserved by standing at $25(\pm 1)°$ C. Three tubes each were taken out on the day of the start of preservation, days 3 and 7 of preservation, and the amount of ATP contained in the cells was quantified by a plate reader (infiniteM200PRO manufactured by Tecan Japan Co., Ltd.) and using CellTiter-Glo reagent (manufactured by Promega Corporation). With the RLU value obtained by measuring on the day of the start of preservation as the standard (cell survival rate 100%), the RLU values obtained by measuring after preservation for each number of days were compared, and the cell survival rate after the lapse of time was calculated, based on which the cell preservability was evaluated. The mean of 3 measurements by the above-mentioned test is shown in Table 4.

TABLE 4

| preserved medium | | DHb086 | Comparative Example 1 | DHb090 | Comparative Example 2 |
|---|---|---|---|---|---|
| concentration (%) of polysaccharide in medium | | 0.016 | 0 | 0.016 | 0 |
| cell survival rate (%) | date of start | 100 | 100 | 100 | 100 |
| | day 3 | 90.0 | 80.9 | 82.0 | 65.3 |
| | day 7 | 66.0 | 35.6 | 57.3 | 34.6 |

From Table 4, DHb086 showed about 70% survival and DHb090 showed about 60% survival even after one week, and the liquid composition containing DAG and ALG showed about twice improved survival rate. Thus, a superior cell preserving effect of the liquid composition containing DAG and ALG was confirmed.

Experimental Example 6

Cell Preservation Test With Varying Cell Seeding Densities and Preservation Temperatures (Cell Type: h-MSC)

Cell suspensions (17 mL) containing human bone marrow-derived mesenchymal stem cells (h-MSC, manufactured by LONZA) ($510 \times 10^4$ cells) were prepared and dispensed into four conical tubes by $3 \times 10^4$ cells (0.1 mL), $30 \times 10^4$ cells (1 mL), $150 \times 10^4$ cells (5 mL), $300 \times 10^4$ cells (10 mL). After centrifugation ($300 \times$ g, 3 min), the supernatant was removed, and a liquid composition containing DAG and ALG (total concentration 0.016 (w/v) %) (DHb086), shown in Table 1, was added and resuspended therein, whereby cell suspensions with each cell density ($1 \times 10^4$ cells/mL, $10 \times 10^4$ cells/mL, $50 \times 10^4$ cells/mL, $100 \times 10^4$ cells/mL) were produced. These were dispensed into 1.5 mL round-bottom micro tubes (24 tubes) by 100 μL each, lid was closed and the suspension was preserved by standing at $25(\pm 1)°$ C. or 37° C. Three tubes each were taken out on the day of the start of preservation, days 1, 3 and 7 of preservation, and the amount of ATP contained in the cells was quantified by a plate reader (infiniteM200PRO manufactured by Tecan Japan Co., Ltd.) and using CellTiter-Glo reagent (manufactured by Promega Corporation). With the RLU value obtained by measuring on the day of the start of preservation as the standard (cell survival rate 100%), the RLU values obtained by measuring after preservation for each number of days were compared, and the cell survival rate after the lapse of time was calculated, based on which the cell preservability was evaluated. The mean of 3 measurements by the above-mentioned test is shown in Table 5.

TABLE 5

| preserved medium | DHb086 | |
|---|---|---|
| concentration (%) of polysaccharide in medium | 0.016 | |
| preservation temperature (° C.) | 25 | 37 |

TABLE 5-continued

| preserved medium | | DHb086 | | | | | | | |
|---|---|---|---|---|---|---|---|---|---|
| cell seeding density (cell/mL) | | $1 \times 10^4$ | $10 \times 10^4$ | $50 \times 10^4$ | $100 \times 10^4$ | $1 \times 10^4$ | $10 \times 10^4$ | $50 \times 10^4$ | $100 \times 10^4$ |
| cell survival rate (%) | date of start | 100 | 100 | 100 | 100 | 100 | 100 | 100 | 100 |
| | day 1 | 89.5 | 111.4 | 85.5 | 80.4 | 59.1 | 65.5 | 38.3 | 31.9 |
| | day 3 | 76.2 | 97.8 | 75.7 | 85.3 | 26.7 | 22.7 | 17.8 | 14.4 |
| | day 7 | 61.1 | 76.2 | 61.0 | 62.1 | 17.9 | 15.6 | 6.7 | 9.8 |

From Table 5, the liquid composition containing DAG and ALG exhibited superior cell preservability at any cell seeding density in the preservation test at 25° C. On the other hand, the survival rate remarkably decreased in the preservation test at 37° C. Therefore, the effectiveness for preservation at ordinary temperature was confirmed.

Experimental Example 7

Preservation of Sphere (Cell Type: h-MSC)

Cell suspensions containing human bone marrow-derived mesenchymal stem cells (h-MSC, manufactured by LONZA) (32.4×10⁴ cells) were prepared, the cell suspension for 32.4×10⁴ cells was added to a 6-well plate for sphere preparation (Elplasia Spheroid Generators MPc500, manufactured by KURARAY CO., LTD.) by 4 mL per 1 well, and cultured for 3 days in a DMEM-Low Glucose medium supplemented with serum under 37° C., 5% carbon dioxide gas conditions to prepare h-MSC spheres. Since the bottom surface of the well has 650 pinholes with diameter 500 μm, seeding was performed at a density of 500 cells per bottom surface of a hanging drop-shaped pinhole, and about 650 spheres formed in each pinhole were obtained. The obtained spheres were collected in 15 mL conical tubes. After centrifugation (100× g, 1 min), the supernatant was removed, and a liquid composition containing DAG and ALG (total concentration 0.020 (w/v) %) (DHb087) (1.3 mL) shown in Table 1 was added and resuspended therein, whereby a sphere suspension (50 spheres/100 μL) was produced. This was dispensed into 1.5 mL round-bottom micro tubes (12 tubes) by 100 μL each, lid was closed and the suspension was preserved by standing at 25(±1)° C. Three tubes each were taken out on the day of the start of preservation, days 3, 5 and 7 of preservation, and the amount of ATP contained in the cells was quantified by a plate reader (infiniteM200PRO manufactured by Tecan Japan Co., Ltd.) and using CellTiter-Glo reagent (manufactured by Promega Corporation). With the RLU value obtained by measuring on the day of the start of preservation as the standard (cell survival rate 100%), the RLU values obtained by measuring after preservation for each number of days were compared, and the cell survival rate after the lapse of time was calculated, based on which the cell preservability was evaluated. The mean of 3 measurements by the above-mentioned test is shown in Table 6. In addition, the appearance of the sphere preserving suspension after standing for 7 days and the sphere observation photograph before and after preservation are shown in FIG. 1.

TABLE 6

| preserved medium | | DHb087 |
|---|---|---|
| concentration (%) of polysaccharide in medium | | 0.020 |
| cell survival rate (%) | date of start | 100.0 |
| | day 3 | 108.6 |
| | day 5 | 106.5 |
| | day 7 | 84.5 |

From Table 6, it was confirmed that the spheres survived without dying even after 5 days of preservation and not less than 80% survived even after 7 days. When preserved in the medium of Comparative Example 1, the spheres were aggregated and the inside of the aggregate developed necrosis, and thus they were excluded from the test (data not shown).

From FIG. 1, it was confirmed that the form of the spheres was maintained before and after preservation, and the spheres maintained the suspended state in the liquid composition containing DAG and ALG even after 7 days of preservation.

Experimental Example 8

Sphere Preservation in Environment With Vibration (Cell Type: h-MSC)

Cell suspensions containing human bone marrow-derived mesenchymal stem cells (h-MSC, manufactured by LONZA) (64.8×10⁴ cells) were prepared, the cell suspension for 32.4×10⁴ cells was added to a 6-well plate for sphere preparation (Elplasia Spheroid Generators MPc500, manufactured by KURARAY CO., LTD.) by 4 mL each in 2 wells, and cultured for 3 days in a DMEM-Low Glucose medium supplemented with serum under 37° C., 5% carbon dioxide gas conditions to prepare h-MSC spheres. Since the bottom surface of the well has 650 pinholes with diameter 500 μm, seeding was performed at a density of 500 cells per bottom surface of a hanging drop-shaped pinhole, and about 650 spheres/well formed in each pinhole were obtained. The obtained spheres were collected per well in a 15 mL conical tube. After centrifugation (100× g, 1 min), the supernatant was removed, and a liquid composition containing DAG and ALG (total concentration 0.020 (w/v) %) (DHb087) (1.3 mL), and a liquid composition free of DAG or ALG (Comparative Example 1) (1.3 mL) for comparison, which are shown in Table 1, were added and resuspended therein, whereby respective sphere suspensions (50 spheres/100 μL) were produced. These were dispensed into 1.5 mL round-bottom micro tubes (12 tubes each) by 100 μL each, lid was closed and the suspension was preserved in a vibrating environment (high-speed shaking apparatus ASCM-1 (mounting tube rack for 1.5 mL, 300 rpm), manufactured by AS ONE) at 25(±1)° C. Three tubes each were taken out on the day of the start of preservation, days 3 and 7 of preservation, and the amount of ATP contained in the cells was quantified by a plate reader (infiniteM200PRO manufactured by Tecan Japan Co., Ltd.) and using CellTiter-Glo reagent (manufactured by Promega Corporation). With the RLU value obtained by measuring on the day of the start of preservation as the standard (cell survival rate 100%), the RLU values obtained by measuring after preservation for each number of days were compared, and the cell survival rate after the lapse of time was calculated, based on which the cell preservability was evaluated. The mean of 3 measurements by the above-mentioned test is shown in Table 7.

TABLE 7

| preserved medium | | Comparative Example 1 | DHb087 |
|---|---|---|---|
| concentration (%) of polysaccharide in medium | | 0 | 0.020 |
| cell survival rate (%) | date of start | 100 | 100 |
| | day 3 | 68.4 | 95.6 |
| | day 7 | 67.8 | 87.9 |

When a preservation test of h-MSC spheres was performed under vibrating conditions assuming the environment during transportation, it was found from Table 7 that the liquid composition containing DAG and ALG exhibited good cell preservability even under vibrating conditions. In Comparative Example 1, the aggregation of the spheres due to the vibration was slightly suppressed but a decrease in the survival rate was observed.

Reference Example 1

Production of Polysaccharide Mixture 1 part by mass or 2 parts by mass of sodium alginate (ALG) (KIMICA ALGIN, manufactured by KIMICA Corporation) and 99 parts by mass or 98 parts by mass of purified water were added to a glass medium bottle, and the mixture was subjected to an autoclave sterilization treatment (121° C., 20 min) to give 1 mass % or 2 mass % concentration of an aqueous ALG solution.

In the same manner, 1 mass % concentration and 2 mass % concentration of aqueous deacylated gellan gum (DAG) (KELCOGEL CG-LA, manufactured by SANSHO Co., Ltd.) solutions were produced.

Given amounts of the aqueous ALG solution and aqueous DAG solution were fractionated into microtubes and carefully mixed by pipetting and homogenized using a disposable syringe with a syringe needle to give a polysaccharide mixture.

Reference Example 2

Production of Liquid Composition (1) Production of Liquid Composition Using Vortex Mixer A given amount of a medium was dispensed to a conical tube (SUMITOMO BAKELITE CO., LTD. 15 mL, 50 mL or 225 mL centrifuge tube) and they were kept under stirring by a vortex mixer while left open. To the medium was vigorously added a given amount of a polysaccharide mixture, the obtained in Reference Example 1, from a disposable syringe (TERUMO CORPORATION TERUMO syringe) with a syringe needle (Fuchigami kikai, FN5200) and filled with the polysaccharide mixture, whereby a liquid composition was produced.

(2) Production of Liquid Composition Using Medium Production Kit (Nissan Chemical Industries, FCeM™-series Preparation Kit)

A given amount of a medium was dispensed to a conical tube (SUMITOMO BAKELITE CO., LTD. 50 mL centrifuge tube) and an adapter cap, which was a constituent of the kit, was set. The tip of a disposable syringe filled with a given amount of a polysaccharide mixture, the obtained in Reference Example 1, was fitted into the cylindrical portion of the adapter cap to establish connection. The plunger of the syringe was pushed manually to vigorously inject the polysaccharide mixture in the syringe into the container, allowing contact with the medium, whereby a liquid composition was produced.

Reference Example 3

Confirmation of Suspending Action

To the liquid composition produced in Reference Example 2 were added polystyrene beads (diameter 500-600 μm, manufactured by Polysciences Inc.) for reproducing suspending cells simulatively and the mixture was stirred. At 10 min from discontinuation of stirring, the dispersion state of the beads in the liquid was confirmed by visual observation. When the sufficient amount of the structure formed by crosslinking of DAG and ALG via a divalent metal cation ($Ca^{2+}$ etc.) is dispersed appropriately finely in the liquid, the beads are also dispersed and suspending in the liquid. On the other hand, when the structure is not sufficiently dispersed, the beads also form sediments accordingly. The dispersion state of the beads is shown with ○ when the beads were preferably dispersed and suspended, Δ when the beads were dispersed with partial formation of sediment, and × when all beads formed sediment.

(1) Suspending Action Using DAG and ALG (1:1)

TABLE 8

| | medium | | | polysaccharide mixture | | | | | |
|---|---|---|---|---|---|---|---|---|---|
| No. | kind | temperature [° C.] | amount added [mL] | 2% DAG [μL] | 1% ALG [μL] | distilled water [μL] | amount added [μL] | addition method | final concentration % DAG/ALG | suspending action |
| B358 | DMEM-low | 4 | 5 | 250 | 500 | 250 | 90 | vortex | 0.009/0.009 | ○ |
| B359 | DMEM-low | 4 | 5 | 250 | 500 | 250 | 80 | vortex | 0.008/0.008 | ○ |
| B360 | DMEM-low | 4 | 5 | 250 | 500 | 250 | 70 | vortex | 0.007/0.007 | ○ |
| B361 | DMEM-low | 4 | 5 | 250 | 500 | 250 | 60 | vortex | 0.006/0.006 | ○ |
| B362 | DMEM-low | 4 | 5 | 250 | 500 | 250 | 50 | vortex | 0.005/0.005 | Δ |

(2) Suspending Action Using DAG and ALG
(0.5:1)

TABLE 9

| | | medium | | polysaccharide mixture | | | | | |
|---|---|---|---|---|---|---|---|---|---|
| No. | kind | temperature [° C.] | amount added [mL] | 1% DAG [μL] | 2% ALG [μL] | amount added [μL] | addition method | final concentration % DAG/ALG | suspending action |
| B363 | DMEM-low | 4 | 5 | 500 | 500 | 75 | vortex | 0.0075/0.015 | ○ |
| B364 | DMEM-low | 4 | 5 | 500 | 500 | 65 | vortex | 0.0065/0.013 | ○ |
| B365 | DMEM-low | 4 | 5 | 500 | 500 | 55 | vortex | 0.0055/0.011 | ○ |
| B366 | DMEM-low | 4 | 5 | 500 | 500 | 50 | vortex | 0.005/0.01 | ○ |
| B367 | DMEM-low | 4 | 5 | 500 | 500 | 45 | vortex | 0.0045/0.009 | ○ |

Reference Example 4

Cell Recovery by Pipetting

Normal human neonatal foreskin skin fibroblasts (NHDF, KURABO INDUSTRIES LTD.) in the logarithmic growth phase ($1800 \times 10^4$ cells) were prepared and dispensed by $300 \times 10^4$ cells. After centrifugation (300× g, 3 min), the supernatant was removed, liquid compositions containing DAG and ALG (total concentration 0.015 (w/v) %) at various ratios (Examples C369 to C373 in Table 10) were added by 30 mL and the mixtures were gently stirred to produce cell suspensions ($10 \times 10^4$ cells/mL). To a 24-well cell culture plate (manufactured by SUMITOMO BAKELITE CO., LTD.) was added a cell suspension ($10 \times 10^4$ cells) by 1 mL per 1 well, and the cells were cultured under 37° C., 5% carbon dioxide gas conditions for 1 week. After culturing, the cell concentration of the cell suspension was measured by a cell counter (TC-20, BIO-RAD), the suspension was transferred to a 1.5 mL microtube and homogenized by 20 times of pipetting using a micropipette (manufactured by Thermo Scientific, clip chip 1000 μL) set to suction/discharge volume 0.2 mL. Thereafter, centrifugation (300× g, 3 min) was performed and the supernatant (1.1 mL) was removed. The cells were resuspended by adding 10% fetal bovine serum-containing DMEM-LG (0.9 mL), and the amount of ATP contained in the cells was quantified by a plate reader (manufactured by Tecan Japan Co., Ltd.) and using CellTiter-Glo (Promega Corporation). With the RLU value obtained by measuring the suspension of the cultured cells before the cell recovery operation as the standard (cell recovery rate 100%), the RLU values obtained by a cell recovery operation with the addition of a suspension inhibitor were compared and the cell recovery rate was calculated. The above test was performed 3 times each, and the mean thereof is shown in the Table.

TABLE 10

| Example | | C369 | C370 | C371 | C372 | C373 |
|---|---|---|---|---|---|---|
| concentration % in medium | ALG | 0.01 | 0.0105 | 0.011 | 0.0115 | 0.012 |
| | DAG | 0.005 | 0.0045 | 0.004 | 0.0035 | 0.003 |
| cell recovery rate % | | 69.6 | 57.1 | 79.4 | 86.3 | 99.4 |

Reference Example 5

Study of Number of Pipettings

Normal human neonatal foreskin skin fibroblasts (NHDF, KURABO INDUSTRIES LTD.) in the logarithmic growth phase ($1440 \times 10^4$ cells) were prepared, suspended in the liquid composition (48 mL) of Example C371 in Table 10, dispensed by $30 \times 10^4$ cells (1 mL) to a 24-well cell culture plate (manufactured by SUMITOMO BAKELITE CO., LTD.), and cultured under 37° C., 5% carbon dioxide gas conditions for 3 days. After culturing, the cell concentration of the cell suspension was measured by a cell counter (TC-20, BIO-RAD), the suspension is was transferred to a 1.5 mL microtube and pipetted a given number of times using a micropipette (manufactured by Thermo Scientific, clip chip 1000 μL) set to suction/discharge volume 0.2 mL. Thereafter, centrifugation (300× g, 3 min) was performed and the supernatant (1.1 mL) was removed. The cells were resuspended by adding 10% fetal bovine serum-containing DMEM-LG (0.9 mL), and the amount of ATP contained in the cells was quantified by a plate reader (manufactured by Tecan Japan Co., Ltd.) and using CellTiter-Glo (Promega Corporation), and the cell recovery rate was calculated. The above test was performed 5 times each, and the mean thereof is shown in the Table.

TABLE 11

| number of pipettings | 3 | 5 | 10 | 15 | 20 |
|---|---|---|---|---|---|
| cell recovery rate % | 44.2 | 69.9 | 70.6 | 68.3 | 75.9 |

Reference Example 6

Addition of Chelating Agent

Normal human neonatal foreskin skin fibroblasts (NHDF, KURABO INDUSTRIES LTD.) in the logarithmic growth phase ($450 \times 10^4$ cells) were prepared, suspended in the liquid composition (15 mL) of Example C371 in Table 10, dispensed by $30 \times 10^4$ cells (1 mL) to a 24-well cell culture plate (manufactured by SUMITOMO BAKELITE CO., LTD.), and cultured under 37° C., 5% carbon dioxide gas conditions for 3 days. After culturing, the cell concentration of the cell suspension was measured by a cell counter (TC-20, BIO-RAD), the suspension was transferred to a 1.5 mL microtube, a given amount of a chelating agent (aqueous mixed solution of EDTA-2Na 0.033 (w/v) % and sodium citrate 0.007 (w/v) %) (0 to 0.1 mL) was added, and pipetted 0 or 10 times using a micropipette (manufactured by Thermo Scientific, clip chip 1000 μL) set to suction/discharge volume 0.2 mL. Thereafter, centrifugation (300× g, 3 min) was performed and the supernatant (1.1 mL) was removed. The cells were resuspended by adding 10% fetal bovine serum-containing DMEM-LG (0.9 mL), and the amount of ATP contained in the cells was quantified by a plate reader (manufactured by Tecan Japan Co., Ltd.) and using CellTiter-Glo (Promega Corporation), and the cell recovery rate was calculated. The above test was performed 3 times each, and the mean thereof is shown in the Table.

TABLE 12

| number of pipettings | 0 | 10 | 10 | 10 |
|---|---|---|---|---|
| amount of chelating agent added mL | 0 | 0 | 0.05 | 0.1 |
| cell recovery rate % | 6.1 | 91.3 | 89.1 | 89.6 |

Experimental Example 7

Proliferation of Jurkat Cell

Normal human T-cell leukemia-derived cells (Jurkat E6.1, DS Pharma Biomedical Co., Ltd.) in the logarithmic growth phase ($240 \times 10^4$ cells) were prepared, centrifuged by $40 \times 10^4$ cells (300× g, 3 min), and the supernatant was removed. Liquid compositions containing DAG and ALG (mass ratio 1:0.5) at various concentrations (Examples DHb020 to DHb023 in Table 13), and a liquid composition containing DAG and not containing ALG (Comparative Example DHb024 in Table 13) were added by 8 mL and the mixtures were gently stirred to produce cell suspensions ($5 \times 10^4$ cells/mL). To a 96-well U-bottom cell culture plate (manufactured by SUMITOMO BAKELITE CO., LTD., MS-309UR) was added a cell suspension ($0.5 \times 10^4$ cells) by 0.1 mL per 1 well, and the cells were cultured under 37° C., 5% carbon dioxide gas conditions for 1 or 4 days. With the cell numbers before and after culturing as the amount of ATP contained in the cells, they were compared by a plate reader (manufactured by Tecan Japan Co., Ltd., infinite M200PRO) and using CellTiter-Glo Luminescent Cell Viability Assay (Promega KK, G7571). The above test was performed 4 times each, and the mean thereof is shown in the Table.

TABLE 13

| | | concentration % in medium | | RLU | | |
|---|---|---|---|---|---|---|
| | | DAG | ALG | before culturing | one day from culturing | 4 days from culturing |
| Comparative Example | DHb024 | 0.020 | 0 | 156639 | 318811 | 1755495 |
| Example | DHb020 | 0.0037 | 0.0073 | 169680 | 351910 | 2068701 |
| | DHb021 | 0.0047 | 0.0093 | 177597 | 362442 | 2107969 |
| | DHb022 | 0.0057 | 0.0113 | 171730 | 313565 | 1973738 |
| | DHb023 | 0.0067 | 0.0133 | 191724 | 332460 | 2016689 |

As a result of evaluation, cell proliferation property equivalent to Comparative Example was achieved even when the medium composition of the present invention was used.

Reference Example 8

A549 Cell Proliferation

Human alveolar basal epithelial glandular cancer cells (A549, DS Pharma Biomedical Co., Ltd.) in the logarithmic growth phase ($86.4 \times 10^4$ cells) were prepared, centrifuged (300× g, 3 min), and the supernatant was removed. Liquid compositions containing DAG and ALG (mass ratio 1:0.5) at various concentrations (Example E041 and Examples E045, E047, E048 in Table 14), and a liquid composition containing DAG and not containing ALG (Comparative Example F049 in Table 14) were added by 8 mL and the mixtures were gently stirred to produce cell suspensions ($5 \times 10^4$ cells/mL). To a 96-well U-bottom cell culture plate (manufactured by SUMITOMO BAKELITE CO., LTD., MS-309UR) was added a cell suspension ($0.5 \times 10^4$ cells) by 0.1 mL per 1 well, and the cells were cultured under 37° C., 5% carbon dioxide gas conditions for 1 or 4 days. With the cell number s before and after culturing as the amount of ATP contained in the cells, they were compared by a plate reader (manufactured by Tecan Japan Co., Ltd., infinite M200PRO) and using CellTiter-Glo Luminescent Cell Viability Assay (Promega KK, G7571). The above test was performed 6 times each, and the mean thereof is shown in the Table.

TABLE 14

| | | concentration % in medium | | RLU | | | |
|---|---|---|---|---|---|---|---|
| | | DAG | ALG | before culturing | one day from culturing | 4 days from culturing | 7 days from culturing |
| Comparative Example | E049 | 0.015 | 0 | 100639 | 114674 | 593527 | 1706412 |
| Example | E045 | 0.002 | 0.004 | 109473 | 127249 | 676181 | 1689925 |
| | E041 | 0.003 | 0.006 | 99532 | 121673 | 595366 | 1738593 |
| | E047 | 0.004 | 0.008 | 101544 | 118188 | 570577 | 1662464 |
| | E048 | 0.005 | 0.010 | 102446 | 120400 | 584303 | 1659677 |

As a result of evaluation, cell proliferation property equivalent to Comparative Example was achieved even when the liquid composition of the present invention was used.

Reference Example 9

Cell Recovery on 10 mL Scale

In the liquid composition (200 mL) of Example E041 in Table 14 were seeded A549 cells at $10 \times 10^4$ cells/mL and the cells were cultured under 37° C., 5% carbon dioxide gas conditions for 2 days. After culturing, the cell suspension was fractionated by 10 mL and a chelating agent (aqueous mixed solution of EDTA-2Na 0.033 (w/v) % and sodium citrate 0.007 (w/v) %) (1 mL) was added. The mixture was immediately passed through a cell strainer (40 μm, 70 μm, 100 μm, Falcon® cell strainer) and centrifuged (3 min) under various conditions (50× g, 100× g, 300× g, g: gravitational acceleration). With the aforementioned cell numbers before and after cell recovery operation as the amount of ATP contained in the cells, they were compared by a plate reader (manufactured by Tecan Japan Co., Ltd., infiniteM200PRO) and using CellTiter-Glo Luminescent Cell Viability Assay (Promega KK, G7571).

TABLE 15

| | gravitational acceleration | cell recovery rate % | | |
|---|---|---|---|---|
| | | 50 | 100 | 300 |
| cell strainer pore size | 40 μm | 73.3 | 92.7 | 96.2 |
| | 70 μm | — | — | 98.6 |
| | 100 μm | — | — | 96.4 |

As a result of evaluation, it was shown that the liquid composition of the present invention can also achieve a high cell recovery rate by passing through a mesh (cell strainer) instead of a pipetting operation.

INDUSTRIAL APPLICABILITY

Using the liquid composition of the present invention, cells and tissues can be preserved for a long term in an unfrozen state at, for example, room temperature and the like while maintaining good survivability. When spheres are preserved in the liquid composition of the present invention, coagulation between the spheres can be avoided, and the development of necrosis in the inside of the spheres can be suppressed.

The contents disclosed in any publication stated in the present specification, including patents, patent applications and scientific literatures, are hereby incorporated in their entireties by reference, to the extent that they have been disclosed herein.

This application is based on patent application No. 2017-173479 filed in Japan, the contents of which are encompassed in full herein.

The invention claimed is:

1. A method for preserving a cell or tissue comprising preserving the cell or tissue in an unfrozen state in a liquid composition comprising deacylated gellan gum or a salt thereof and alginic acid or a salt thereof.

2. The method according to claim 1, wherein the cell or tissue is preserved in a suspended state in the liquid composition.

3. The method according to claim 1, wherein the cell or tissue is preserved at 1° C.-30° C.

4. The method according to claim 1, wherein the cell or tissue is preserved in a closed container.

5. The method according to claim 1, wherein the cell or tissue is preserved during vibration.

6. The method according to claim 1, wherein the cell to be preserved is in a sphere state.

* * * * *